(12) United States Patent
Duck et al.

(10) Patent No.: US 9,149,423 B2
(45) Date of Patent: *Oct. 6, 2015

(54) INGESTIBLE EVENT MARKERS COMPRISING AN INGESTIBLE COMPONENT

(75) Inventors: Robert Duck, San Francisco, CA (US); George Savage, Portola Valley, CA (US); Patricia Johnson, Palo Alto, CA (US); Mark Zdeblick, Portola Valley, CA (US); Benedict Costello, Berkeley, CA (US); Kityee Au-Yeung, San Francisco, CA (US); Timothy Robertson, Belmont, CA (US); Hooman Hafezi, Redwood City, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/319,977

(22) PCT Filed: May 10, 2010

(86) PCT No.: PCT/US2010/034186
§ 371 (c)(1),
(2), (4) Date: Nov. 10, 2011

(87) PCT Pub. No.: WO2010/132331
PCT Pub. Date: Nov. 18, 2010

(65) Prior Publication Data
US 2012/0059257 A1    Mar. 8, 2012

Related U.S. Application Data

(60) Provisional application No. 61/177,611, filed on May 12, 2009.

(51) Int. Cl.
A61K 9/00 (2006.01)
A61K 9/48 (2006.01)
(Continued)

(52) U.S. Cl.
CPC .............. *A61K 9/0004* (2013.01); *A61B 5/073* (2013.01); *A61B 5/1473* (2013.01); *A61K 9/4808* (2013.01); *A61K 49/00* (2013.01); *A61M 31/002* (2013.01); *A61J 3/07* (2013.01)

(58) Field of Classification Search
CPC ............................. A61M 31/002; A61J 3/07
USPC .................................. 128/920; 600/300, 431
See application file for complete search history.

(56) References Cited

U.S. PATENT DOCUMENTS 3,589,943 A    6/1971    Grubb et al.
3,607,788 A    9/1971    Adolph
(Continued)

FOREIGN PATENT DOCUMENTS

DE    10313005    10/2004
EP    0344939    12/1989
(Continued)

OTHER PUBLICATIONS

Dipole antenna in NPL__AntennaBasics.pdf.*
(Continued)

*Primary Examiner* — Long V Le
*Assistant Examiner* — Ellsworth Weatherby
(74) *Attorney, Agent, or Firm* — K&L Gates LLP

(57) ABSTRACT

Ingestible event markers comprising an identifier and an ingestible component are provided. The ingestible component may vary, where ingestible components of interest include osmotic ingestible components, liquid capsules, tablets, multi-layered ingestible component and multi-compartment ingestible components. In some instances, the identifier is mechanically stably associated with the ingestible component. Also provided are systems that include the ingestible event markers, as well as methods of using the ingestible event markers.

20 Claims, 10 Drawing Sheets

(51) Int. Cl.
  *A61K 49/00*  (2006.01)
  *A61B 5/07*  (2006.01)
  *A61M 31/00*  (2006.01)
  *A61B 5/1473*  (2006.01)
  *A61J 3/07*  (2006.01)

(56) References Cited

U.S. PATENT DOCUMENTS

| | | |
|---|---|---|
| 3,642,008 A | 2/1972 | Bolduc |
| 3,679,480 A | 7/1972 | Brown et al. |
| 3,682,160 A | 8/1972 | Murata |
| 3,719,183 A * | 3/1973 | Schwartz ............... 600/302 |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,844,076 A | 7/1989 | Lesho |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A * | 3/1991 | Eckenhoff et al. ............ 424/438 |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,485,841 A | 1/1996 | Watkin et al. |
| 5,567,210 A | 10/1996 | Bates et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,705,189 A | 1/1998 | Lehmann et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,925,030 A | 7/1999 | Gross et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,038,464 A | 3/2000 | Axelgaard et al. |
| 6,042,710 A | 3/2000 | Dubrow |
| 6,047,203 A | 4/2000 | Sackner |
| 6,068,589 A | 5/2000 | Neukermans |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Nohl et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,564,079 B1 | 5/2003 | Cory |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 * | 7/2003 | Faour ................. 604/892.1 |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |

(56) References Cited

U.S. PATENT DOCUMENTS

| | | |
|---|---|---|
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 * | 8/2008 | Kroll et al. ............... 340/573.1 |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 8,036,731 B2 | 10/2011 | Kimchy et al. |

(56) References Cited

U.S. PATENT DOCUMENTS

| | | |
|---|---|---|
| 8,389,003 B2 | 3/2013 | Mintchev et al. |
| 8,425,492 B2 | 4/2013 | Herbert et al. |
| 8,597,186 B2 | 12/2013 | Hafezi et al. |
| 8,698,006 B2 | 4/2014 | Bealka et al. |
| 8,758,237 B2 | 6/2014 | Sherman et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032384 A1* | 3/2002 | Raymond et al. ............ 600/513 |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |

(56) References Cited

U.S. PATENT DOCUMENTS

| | | |
|---|---|---|
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1* | 12/2006 | Mercure et al. ............... 235/435 |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical et al. |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2005/0092108 A1 | 5/2008 | Andermo |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |
| 2009/0082645 A1* | 3/2009 | Hafezi et al. ............... 600/302 |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |

(56) References Cited

U.S. PATENT DOCUMENTS

| | | |
|---|---|---|
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1* | 7/2010 | Robertson et al. ............ 600/117 |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0239616 A1 | 9/2010 | Hafezi et al. |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1* | 11/2010 | Kauffman et al. ............ 340/665 |
| 2010/0297640 A1 | 11/2010 | Kumar et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0062371 A1 | 3/2012 | Radivojevic et al. |
| 2012/0299723 A1 | 11/2012 | Hafezi et al. |

FOREIGN PATENT DOCUMENTS

| | | |
|---|---|---|
| EP | 1246356 | 10/2002 |
| EP | 1534054 | 5/2005 |
| EP | 1702553 | 9/2006 |
| EP | 1789128 | 5/2007 |
| EP | 2143369 | 1/2010 |
| JP | 61072712 | 4/1986 |

(56) References Cited

FOREIGN PATENT DOCUMENTS

| | | |
|---|---|---|
| JP | 05-228128 | 9/1993 |
| JP | 2000-506410 | 5/2000 |
| JP | 2002263185 | 9/2002 |
| JP | 2002282219 | 10/2002 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005343515 | 12/2005 |
| JP | 2006006377 | 1/2006 |
| JP | 2006509574 | 3/2006 |
| JP | 2007-313340 | 12/2007 |
| JP | 2008011865 | 1/2008 |
| KR | 2006077523 | 7/2006 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9739963 | 10/1997 |
| WO | WO9843537 | 10/1998 |
| WO | WO9937290 | 7/1999 |
| WO | WO9937920 | 7/1999 |
| WO | WO9959465 | 11/1999 |
| WO | WO0033246 | 6/2000 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005047837 | 5/2005 |
| WO | WO2005051166 | 6/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006046648 | 5/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Gaglani S. "Put Your Phone, or Skin, on Vibrate" MedGadget (2012) http://medgadget.com/2012/03/put-your-phone-or-skin-on-vibrate.html 8pp.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Rolison et al., "Electrically conductive oxide aerogels: new materials in electrochemistry" J. Mater. Chem. (2001) 1, 963-980.

AADE, "AADE 37th Annual Meeting San Antonio Aug. 4-7, 2010" American Association of Diabetes Educators (2010); http://www.diabeteseducator.org/annualmeeting/2010/index.html; 2 pp.

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. for Gastrointestinal Endoscopy (2006) vol. 63, No. 4; 7 pp.

(56) References Cited

OTHER PUBLICATIONS

Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Coury, L. "Conductance Measurement Part 1: Theory"; Current Separations, 18:3 (1999) p. 91-96.
Delvaux et al., "Capsule endoscopy: Technique and indications" Clinical Gastoenterology (2008) vol. 22, Issue 5, pp. 813-837.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research Pier 59, 1-15 (2006).
Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
ISFET—Ion Sensitive Field-Effect Transistor; Microsens S.A. pdf document. First cited by Examiner in Office Action dated Jun. 13, 2011 for U.S. Appl. No. 12/238,345; 4pp.
INTROMEDIC, MicroCam Innovative Capsule Endoscope Pamphlet. (2006) 8 pp (http://www.intromedic.com/en/product/productinfo.asp).
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Li, P-Y, et al. "An electrochemical intraocular drug delivery device", Sensors and Actuators A 143 (2008) p. 41-48.
LIFESCAN, "OneTouch UltraLink™" http://www.lifescan.com/products/meters/ultralink (2010) 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
MEDTRONIC, "CareLink Therapy Management Software for Diabetes" (2010); https://carelink.minimed.com/patient/entry.jsp?bhcp=1; 1 pp.
MEDTRONIC, "Carelink™ USB" (2008) http://www.medtronicdiabetes.com/pdf/carelink_usb_factsheet.pdf 2pp.
MEDTRONIC "The New MiniMed Paradigm® Real-Time Revel™ System" (2010) http://www.medtronicdiabetes.com/products/index.html; 2 pp.
MEDTRONIC, "Mini Med Paradigm® Revel™ Insulin Pump" (2010) http://www.medtronicdiabetes.com/products/insulinpumps/index.html; 2 pp.
MEDTRONIC, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
Minimitter Co. Inc. VitalSense Integrated Physiological Monitoring System. Product Description. (2005).
Minimitter Co. Inc. VitalSense Wireless Vital Signs Monitoring. Temperatures.com Mar. 31, 2009.
Mohaverian et al., "Estimation of gastric residence time of the Heidelberg capsule in humans: effect of varying food composition" Gastroenterology (1985) 89:(2): 392-7.
"New 'smart pill' to track adherence" E-Health-Insider (2010) http://www.e-health-insider.com/news/5910/new_'smart_pill'_monitors_medicines.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Philips Respironics (http/minimitter.com/products.cfm) Products, Noninvasive Technology to Help Your Studies Succeed. 510(k) Permanent Notification for Vital Sense. Apr. 22, 2004.
"RFID "pill" monitors marchers" RFID News (2008) http://www.rfidnews.org/2008/07/23/rfid-pill-monitors-marchers/.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

(56) References Cited

OTHER PUBLICATIONS

"Smartlife awarded patent for knitted transducer" Innovation in Textiles News: http://www.innovationintextiles.com/articles/208.php; 2pp. (2009).

"The SmartPill Wireless Motility Capsule" SMARTPILL, The Measure of GI Health; (2010) http://www.smartpillcorp.com/index.cfm?pagepath=Products/The_SmartPill_Capsule &id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

University of Florida News "Rx for health: Engineers design pill that signals it has been swallowed" (2010) 2pp.; http://news.ufl.edu/2010/03/31/antenna-pill-2/.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; First cited by Examiner in Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Zworkin, "A Radio Pill" Nature, (1957) 898, 179 Nature Publishing Group.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Kim et al., "A Semi-Interpenetrating Network System for a Polymer Membrane"; Eur. Polym. J. vol. 33 No. 7; pp. 1009-1014 (1997).

* cited by examiner

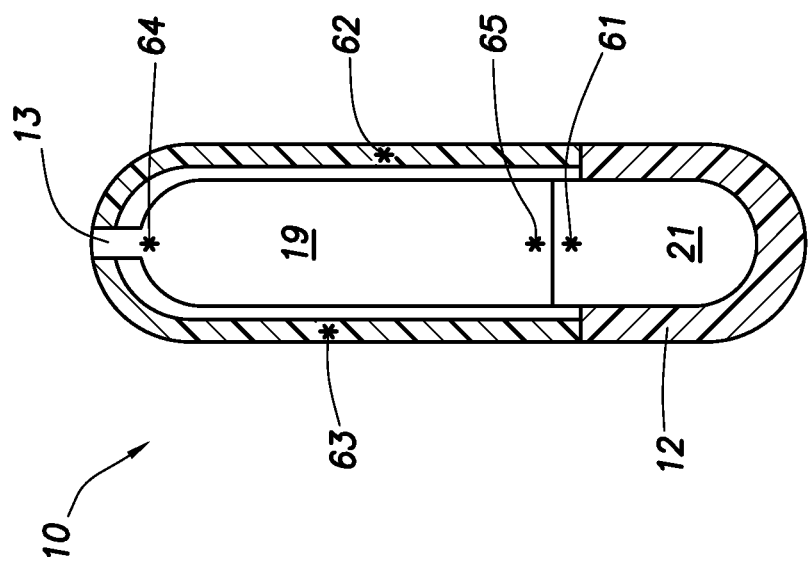
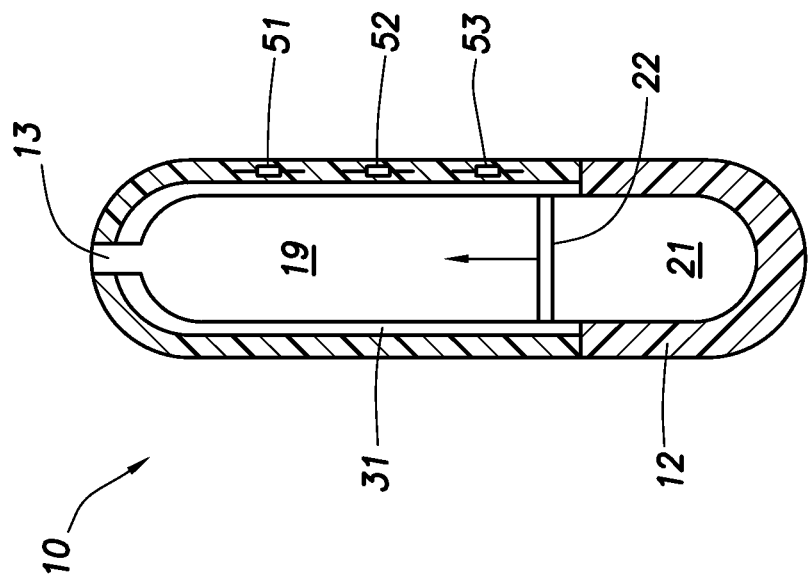

INGESTIBLE EVENT MARKERS COMPRISING AN INGESTIBLE COMPONENT

This application claims priority to International Patent Application No. PCT/US2010/034186, filed May 10, 2010 and titled "Ingestible Event Markers Comprising An Ingestible Component," which application claims the benefit of prior U.S. Provisional Patent Application No. 61/177,611, filed May 12, 2009 and titled "Ingestible Event Markers Comprising an Identifier and an Ingestible Component", which patent applications are incorporated herein by reference for all purposes.

INTRODUCTION

Prescription medications are effective remedies for many patients when taken properly, e.g., according to instructions. However, studies have shown that, on average, about 50% of patients do not comply with prescribed medication regimens. A low rate of compliance with medication regimens results in a large number of hospitalizations and admissions to nursing homes every year. In the United States alone, it has recently been estimated that the cost to the resulting from patient non-compliance is reaching $100 billion annually.

Consequently, various methods and apparatus have been made available to improve patient compliance with pre-scribed regimens in efforts to improve patient health. To date, many different types of "smart" packaging devices have been developed. In some cases, such devices automatically dispense an appropriate medication. In other cases, there are electronic controls that detect and record when a medication is removed from its packaging.

While devices and protocols have been developed for improving patient compliance, there is continued interest in the development of new ways of monitoring patient compliance. It would be an important advancement in clinical medicine if the actual administration and ingestion of a pharmaceutical, such as a pill being dissolved in the stomach, could be monitored in an automatic and accurate manner without dependence on patient or medical staff reporting.

SUMMARY

Event markers, e.g., ingestible event markers comprising an ingestible component are provided. The ingestible component may vary, where ingestible components of interest include osmotic ingestible components, liquid capsules, tablets, multi-layered ingestible component and multi-compartment ingestible components. In some instances, the ingestible event marker is mechanically stably associated with the ingestible component. Also provided are systems that include the ingestible event markers, as well as methods of using the ingestible event markers.

BRIEF DESCRIPTION OF THE FIGURES

FIG. 5 provides a view of multiple ingestible event markers integrated in the semipermeable wall of an osmotic capsule.

FIG. 6 provides a view of an ingestible event marker where different potential locations are shown on an osmotic capsule.

DETAILED DESCRIPTION

Figure 1A:
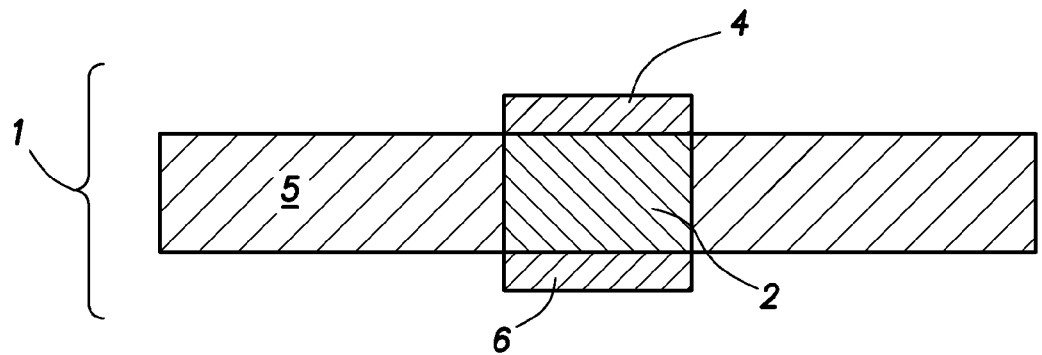
FIGS. 1A and 1B provide views of various configurations according to different aspects of the invention.

Event markers, e.g., ingestible event markers ("IEMs"), sometimes referred to herein as "identifiers", and associated ingestible component are provided. The ingestible component may vary, where ingestible components of interest include osmotic ingestible components, liquid capsules, tablets, multi-layered ingestible component and multi-compartment ingestible components. In some instances, the ingestible event marker is mechanically stably associated with the ingestible component. Also provided are systems that include the ingestible event markers, as well as methods of using the ingestible event markers.

Ingestible Event Markers

An ingestible event marker (IEM) is a device that is dimensioned to be ingestible and includes an identifier circuitry component and, optionally, an amplifier or current path extender.

To illustrate, various aspects of the IEM may comprise a support, a control circuit physically associated with the support to control the IEM, a first electrochemical material physically associated with the support and electrically coupled to the control circuit, a second electrochemical material electrically coupled to the control circuit and physically associated with the support at a location different from the location of the first material.

Upon ingestion, the IEM contacts a conducting fluid, e.g., stomach fluid. The conducting fluid activates the IEM and the first and second electrochemical materials provide a voltage potential difference. In various aspects, the control circuit controls the conductance through logic that alters the overall impedance of the system. The control circuit, for example, may be electrically coupled to a clock. The clock may provide a clock cycle to the control circuit. Based upon the programmed characteristics of the control circuit, when a set number of clock cycles have passed, the control circuit alters the conductance characteristics between electrochemical materials. This cycle may be repeated and thereby the control circuit may produce a unique current signature characteristic, sometimes referred to herein as a "current signature". The control circuit may also be electrically coupled to a memory. Both the clock and the memory may be powered by the voltage potential created between the materials when in contact with a conducting fluid.

Thus, in some instances, the two dissimilar electrochemical materials serve as a cathode and an anode. When the two dissimilar electrochemical materials come in contact with the body fluid, such as stomach fluid, a potential difference (voltage) is generated between the cathode and the anode as a result of the respective oxidation and reduction reactions occurring at the two dissimilar electrochemical materials. The dissimilar electrochemical materials making up the electrochemical materials can be made of any two materials appropriate to the environment in which the IEM circuitry component will be operating. The active materials are any pair of materials with different electrochemical potentials. The electrochemical material materials may be chosen to provide for a voltage upon contact with the target physiological site. Where desired, the voltage provided by the two dissimilar electrochemical materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Anode materials of interest include, but are not limited to: magnesium, zinc, sodium, lithium, iron and alloys thereof, e.g., Al and Zn alloys of Mg, which may or may not be intercalated with a variety of materials such, as graphite with Li, K, Ca, Na, Mg, and the like. Cathode materials of interest include, but are not limited to, copper salts, such as copper salts of iodide, chloride, bromide, sulfate, formate, $Fe^{3+}$ salts, e.g., orthophosphate, pyrophosphate, etc. One or both of the metals may be doped with a non-metal, for example to enhance the voltage output of the battery. Non-metals that may be used as doping agents in certain aspects include, but are not limited to: sulfur, iodine and the like. In certain aspects, the electrode materials are cuprous iodine (CuI) or cuprous chloride (CuCl) as the anode and magnesium (Mg) metal or magnesium alloy as the cathode. Aspects of the present invention use electrode materials that are not harmful to the human body.

With respect to current signatures, the current signatures may distinguish one class of highly reliable event marker from other types or may be universally unique, such as where the current signature is analogous to a human fingerprint which is distinct from any other fingerprint of any other individual and therefore uniquely identifies an individual on a universal level. In various aspects, the control circuit may generate a variety of different types of communications, including but not limited to: RF signals, magnetic signals, conductive (near field) signals, acoustic signals, etc.

In various aspects, the IEM may further comprise a membrane which, for example, produces a virtual dipole length between the pair of transmission elements that is larger than the actual dipole length. In addition to controlling the magnitude of the current path between the materials, a membrane (sometimes referred to herein as "amplifier" or "skirt") is used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, and in the U.S. patent application Ser. No. 12/564, 017 entitled, "Communication System with Partial Power Source" filed Sep. 21, 2009 the entire content of which are incorporated herein by reference.

Receivers, sometimes referred to herein as a "detector" may detect the communication, e.g., current. Receivers may not require any additional cable or hard wire connection between the device and a receiver of the communication, sometimes referred to herein as a detector.

In addition to the IEM, aspects also include an ingestible component with which the IEM is stably associated in some manner. By "stably associated" is meant that the IEM and the ingestible component, e.g., a vehicle, do not separate from each other, at least until administered to the subject in need thereof, e.g., by ingestion. As the IEMs are dimensioned to be ingestible, they are sized so that they can be placed in a mammalian, e.g., human or animal, mouth and swallowed. In some instances, IEMs of the invention have a longest dimension that is 30 mm or less, such as 20 mm or less, including 5 mm or less.

Various aspects of ingestible event markers of interest are described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/ 022257 published as WO/2008/066617; PCT application serial no. PCT/US2008/052845 published as WO/2008/ 095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/ US2008/077753 published as WO2009/042812; the disclosures of which are herein incorporated by reference.

In certain aspects, the ingestible event markers are disrupted upon administration to a subject. As such, in certain aspects, the compositions are physically broken, e.g., dissolved, degraded, eroded, etc., following delivery to a body, e.g., via ingestion, injection, etc. The compositions of these aspects are distinguished from devices that are configured to be ingested and survive transit through the gastrointestinal tract substantially, if not completely, intact.

IEMs may be fabricated using any convenient protocol. IEM fabrication protocols of interest include, but are not limited to, those described in PCT application serial no. PCT/ US2006/016370 published as WO/2006/116718; PCT application serial no. PCT/US2007/082563 published as WO/2008/052136; PCT application serial no. PCT/US2007/ 024225 published as WO/2008/063626; PCT application serial no. PCT/US2007/022257 published as WO/2008/ 066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/ 056299 published as WO/2008/112578; and PCT application serial no. PCT/US2008/077753; the disclosures of which are herein incorporated by reference.

Figure 1B:
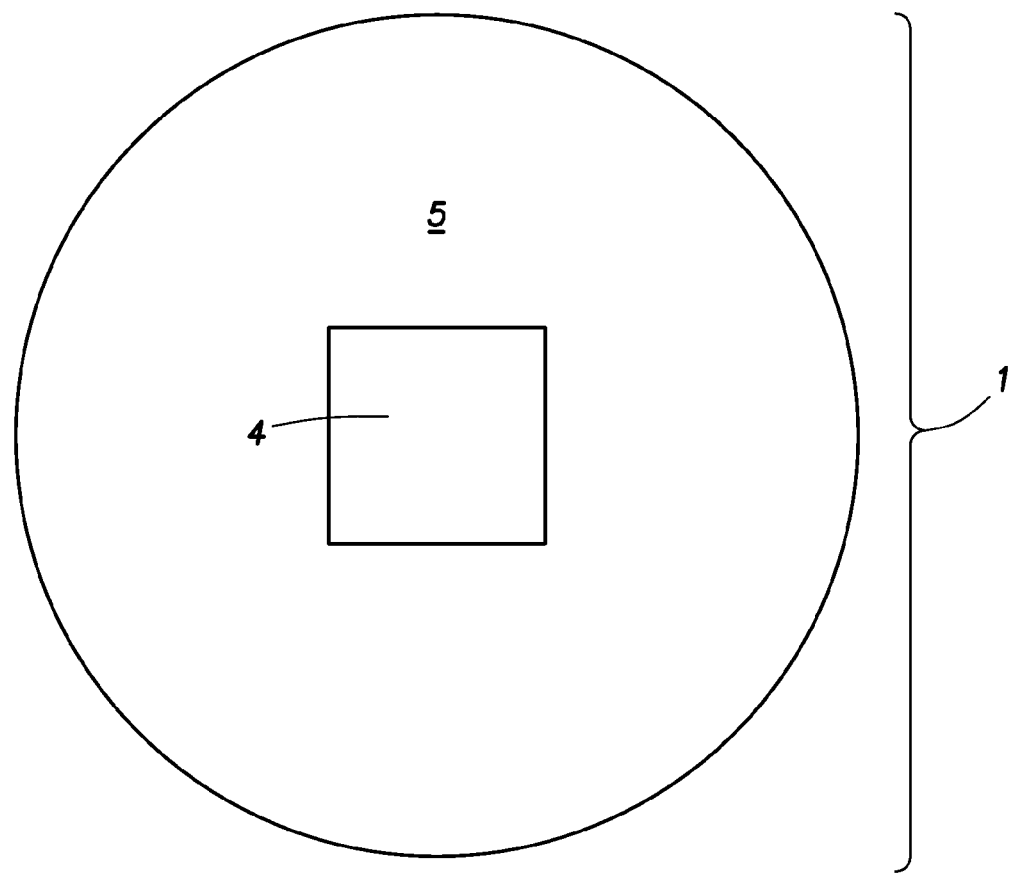

FIG. 1A provides a view of an aspect of an IEM according to the invention which has a membrane that extends beyond the outer edges of the signal transmission elements to provide a virtual dipole having a length that is longer than the actual dipole between the signal transmission elements. As shown in FIG. 1A, IEM 1 includes integrated circuit 2, having a first electrochemical material 4 (which may comprise two distinct material layers) and a second electrochemical material 6. Also shown is disc shaped membrane 5. FIG. 1B provides an overhead view of the IEM shown in FIG. 1A, showing the disc shape of first electrochemical material 4 and the positioning of the first electrochemical material in the center of disc shaped membrane 5. The distance that the edge of the membrane may extend beyond the edge of electrodes may vary, and in certain aspects is 0.05 mm or more, e.g., 0.1 mm or more, including 1.0 mm or more, such as 5.0 mm or more and including 10 mm or more, where the distance may not exceed 100 mm in certain aspects.

As can be seen in the aspect depicted in FIGS. 1A to 1B, the first and second electrochemical materials may have any convenient shape, e.g., square, disc, etc. The disc shaped membrane 5 is a planar disc structure, where the edge of the membrane extends beyond the edge of the planar the first and second electrochemical materials. In the depicted aspect, the radius of the membrane is longer than the radius of the first and second electrochemical materials, e.g., by 1 mm or more, such as by 10 mm or more.

Membranes may have "two-dimensional" or "three-dimensional" configurations, as desired. Membrane configurations of interest are further described in PCT application serial no. US2008/077753 published as WO2009/042812, as well as U.S. provisional application Ser. Nos. 61/142,849 and 61/173,511; the disclosures of which are herein incorporated by reference.

The membrane may be fabricated from a number of different materials, where the membrane may be made of a single material or be a composite of two or more different types of materials, as developed in greater detail below. In certain instances, the membrane will have a mechanical strength sufficient to withstand the mechanical forces typical of the gastrointestinal (GI) tract without folding onto itself and losing its shape. This desired mechanical strength may be chosen to last for at least the duration of the communication, which may be 1 second or longer, such as at least 1 minute or longer, up to 6 hours or longer. In certain aspects, the desired mechanical strength is selected to least for a period of time ranging from 1 to 30 minutes. The desired mechanical strength can be achieved by proper selection of polymer and/or fillers, or mechanical design (e.g., lamination of multiple layers, or curvature of the amplifier surface) to increase the mechanical strength of the final structure.

Membranes of the invention are ones that are electrically insulating. As such, the materials from which the membranes are fabricated are electrically insulating materials. A given material is electrically insulating if it has a resistivity that is two times or greater than the medium in which the device operates, e.g., stomach fluid, such as ten times or greater, including 100 times or greater than the medium in which the device operates.

Ingestible Component

As summarized above, various aspects of the invention include one or more IEMs physically associated with an ingestible component. The ingestible components are compositions that are ingestible. Solid ingestible component configuration formats include tablet and capsule configurations. While the ingestible component may have a solid configuration, the solid configuration may include a liquid component, such as is present in a liquid capsule. In some instances, the ingestible component is configured to impart a controlled release profile to an active agent that is associated with the IEM. Ingestible components of interest can be found in Remington's Pharmaceutical Sciences, Mace Publishing Company, Philadelphia, Pa., 17th ed. (1985). Three types of ingestible components of interest are: 1) osmotic ingestible components; 2) liquid capsules; and 3) ingestible components in which the IEM is mechanically stably associated with the ingestible component. Each of these configurations of interest is now described in greater detail.

Osmotic Ingestible Component

Aspects of the invention include IEMs in which one or more IEMs are stably associated with an ingestible component that is an osmotic ingestible component. Of interest are osmotic ingestible components that exhibit a controlled release profile, such as an extended release profile or other release profile, as desired. Osmotic ingestible components are ingestible components that include an osmotic member. By osmotic member is meant a component that that is fabricated from a material which absorbs, i.e., imbibes, liquid by osmosis and in doing so, either alone or in conjunction with other components of the IEM, at least modulates release of an active agent from the IEM. Osmotic ingestible components may have a variety of different configurations, including capsule configurations, tablet configurations, etc. In certain instances, osmotic ingestible components include a semipermeable layer (for example a coating or membrane), an osmotic member, and one or more stably associated IEMs. Semipermeable layers and osmotic members are further described below in conjunction with osmotic capsule aspects. However, while osmotic capsules are described in greater detail below, of interest are all osmotic ingestible components that include an osmotic member, a semipermeable layer and an IEM.

Osmotic ingestible components of interest include, but are not limited to: osmotic capsules. FIG. 2A shows an example of an osmotic ingestible component that has a capsule configuration. In FIG. 2A, osmotic capsule 10, is seen in closed view, comprising a body 11, a wall 12 and passageway 13. Wall 12 surrounds and forms an internal space, not seen in FIG. 2A. Osmotic capsule 10 has a first end 9 with passageway 13 and a second end 8.

Figure 2B:
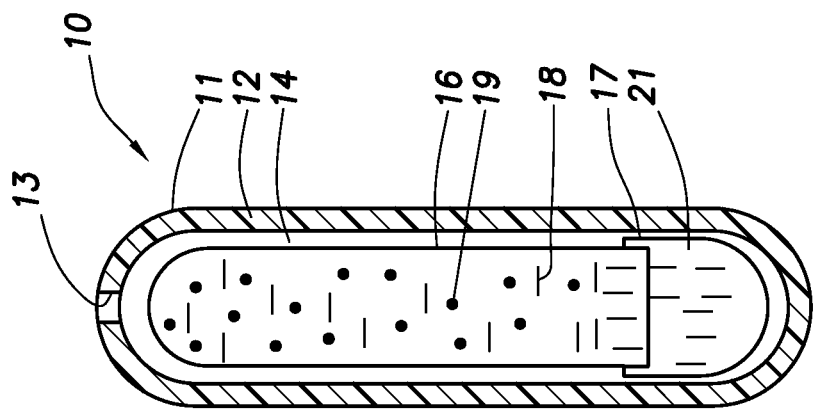
FIGS. 2A to 2D provide views of different osmotic capsule configurations.
Figure 2A:
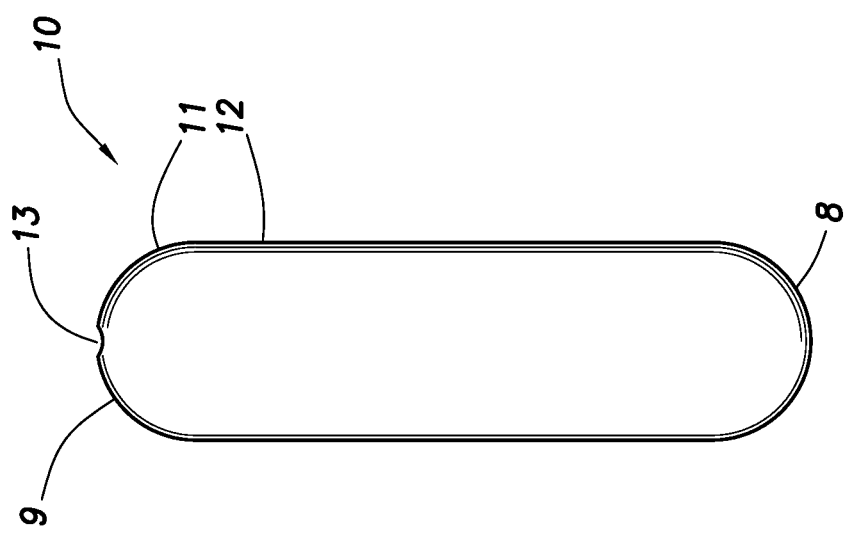

In FIG. 2B, osmotic capsule 10 is shown having body 11, wall 12 that surrounds and forms internal space 14. Wall 12 comprises passageway, i.e., orifice, 13 that connects internal space 14 with the exterior environment of the osmotic capsule 10. Internal space 14 holds and stores a capsule comprising a body section 16 and a cap section 17. These sections may be fabricated from any convenient material, such as hydroxypropylmethylcellulose (HPMC). The body section 16 is a component receiving section that is filled with an active agent composition 19 which may include a pharmaceutically acceptable carrier, 18. The pharmaceutically acceptable carrier 18 can be initially dry, or initially wet. An osmotic member 21, such as an expandable hydrophilic polymer as described in greater detail below, is present in the open end of body 16 and closed by sliding cap 17 over body section 16. In those instances where body 16 comprises a dry active agent 19 composition, a solution or a suspension is formed in the capsule by fluid being imbibed from the environment into the capsule for mixing with the active agent in situ. As shown in FIG. 2B, the osmotic capsule 10 is composed of two sections fitted together by slipping or telescoping the cap section over the body section. This configuration provides a closed capsule in which the capsule wall surrounds and encapsulates the active agent composition 19. The capsule composed of two sections defines a hard capsule.

Osmotic capsule 10 comprises an osmotic member 21 that expands in the presence of imbibed aqueous and biological fluids. Body 16 comprising osmotic member 21 is closed by cap 17, to provide a closed capsule. Osmotic member 21 provides an expandable push driving force that acts to deliver the active agent 19 from the osmotic capsule 10. Osmotic member 21 exhibits fluid imbibing and/or absorbing properties. Osmotic member 21 may include a hydrophilic polymer that can interact with water and aqueous biological fluids and then swell or expand. The hydrophilic polymers are known also as osmopolymers, osmogels and hydrogels, and they exhibit a concentration gradient across wall 12, whereby they imbibe fluid into osmotic capsule 10. Hydrophilic polymers of interest include, but are not limited to: poly(alkylene oxide)

of 10,000 to 10,000,000 weight-average molecular weight including poly(ethylene oxide), and an alkali carboxymethylcellulose of 10,000 to 6,000,000 weight average molecular weight including sodium carboxymethylcellulose. Osmotic member 21 may include 10 mg to 425 mg of osmopolymer. Osmotic member 21 may include 1 mg to 50 mg of a poly(cellulose) of a member selected from the group consisting of hydroxyethylcellulose, hydroxyproylcellulose, hydroxypropylmethylcellulose, and hydroxypropylbutylcellulose. Osmotic member 21 may include 0.5 mg to 175 mg of an osmotically effective solute (known also as osmotic solute and osmagent) that imbibes fluid through wall 12 into osmotic capsule 10. The osmotically effective solutes may be selected from the group consisting of a salt, acid, amine, ester and carbohydrate. Osmagents of interest include, but are not limited to: magnesium sulfate, magnesium chloride, potassium sulfate, sodium sulfate, lithium sulfate, potassium acid phosphate, mannitol, urea, inositol, magnesium succinate, tartaric acid, sodium chloride, potassium chloride, and carbohydrates such as raffinose, sucrose, glucose, lactose, and sorbitol. Osmotic member 21 may also include 0 wt % to 3.5 wt % of a colorant, such as ferric oxide.

Osmotic capsule 10 includes a wall 12 that surrounds the internal capsule produced by 16 and 17. Wall 12 may be fabricated from a composition permeable to the passage of fluid, aqueous and biological fluid, present in environment of use. In addition, wall 12 is substantially impermeable to the passage of active agent composition 19. Wall 12 is nontoxic, and it maintains its physical and chemical integrity during the active agent delivery from the osmotic capsule 10. Materials of interest for forming wall 12 include, but are not limited to: semipermeable polymers, semipermeable homopolymers, semipermeable copolymers, and semipermeable terpolymers. Polymers of interest include cellulose esters, cellulose ethers, and cellulose ester-esters. These cellulosic polymers may have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, and semipermeable polymer forming groups.

The semipermeable materials may include a member selected from the group consisting of cellulose acylate, cellulose diacylate, cellulose triacetate, cellulose acetate, cellulose diacetate, cellulose triacetate, mono-, di- and tri-cellulose alkanylates, mono-, di-, and tri-alkenylates, mono-, di-, and tri-aroylates, and the like. Polymers of interest include cellulose acetates having a D.S. of 1.8 to 2.3 and an acetyl content of 32 to 39.9%; cellulose diacetates having a D.S. of 1 to 2 and an acetyl content of 21 to 35%; cellulose triacetates having a D.S. of 2 to 3 and an acetyl content of 34 to 44.8%; and the like. More specific cellulosic polymers of interest include cellulose proprionates having a D.S. of 1.8 and a propionyl content of 38.5%; cellulose acetate propionates having an acetyl content of 1.5 to 7% and an acetyl content of 39 to 42%; cellulose acetate propionates having an acetyl content of 2.5 to 3%, an average propionyl content of 39.2 to 45% and a hydroxyl content of 2.8 to 5.4%; cellulose acetate butyrates having a D.S. of 1.8, an acetyl content of 13 to 15%, and a butyryl content of 34 to 39%; cellulose acetate butyrates having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, celluloser acetate succinate, cellulose propionate succinate, cellulose acetate octanoate, cellulose valerate palmitate, cellulose acetate heptonate, cellulose valerate palmitate, cellulose acetate heptonate, and the like.

Additional semipermeable polymers include cellulose acetaldehyde dimethyl acetate; cellulose acetate ethylcarbonate; cellulose acetate methylcarbamate; cellulose dimethylaminoacetate; semipermeable polyamides; semipermeable polyurethanes; semipermeable sulfonated polystyrenes; cross-linked, selectively semipermeable polymers formed by the coprecipitation of a polyanion and a polycation; semipermeable polystyrene derivatives; semipermeable poly(sodium styrenesulfonate); semipermeable poly(vinylbenzyltrimethyl)ammonium chloride; semipermeable polymers exhibiting a fluid permeability of 10 to 10 (cc·mil/cm·hr·atm) expressed as per atmosphere of hydrostatic or osmotic pressure difference across a semipermeable wall.

Figure 2D:
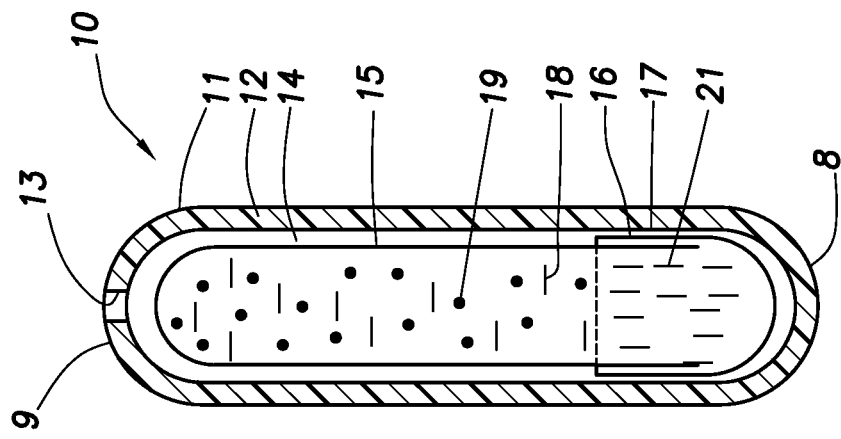
Figure 2C:
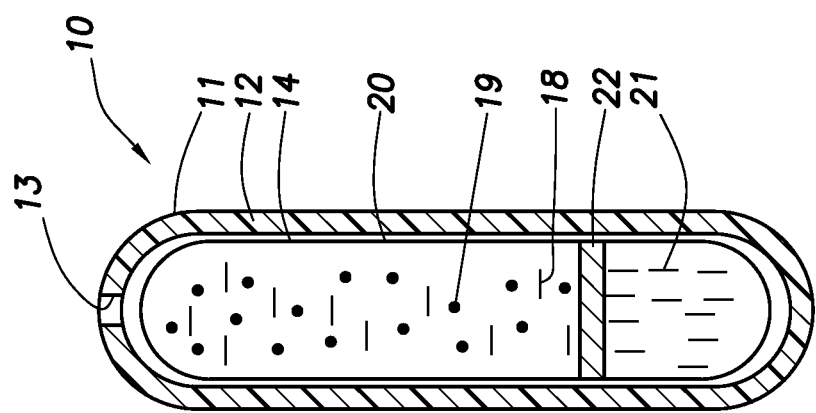

FIG. 2C illustrates another osmotic capsule 10 configuration of interest. In FIG. 2C, osmotic capsule 10 includes a body 11, comprising wall 12 with a passageway 13. Wall 12 surrounds and defines internal compartment 14 housing internal capsule 20. Internal capsule 20 in its final manufacture comprises a one piece capsule that distinguishes capsule 20 from the two piece capsule presented above in FIG. 2B. Capsule 20 comprises active agent composition 19. Capsule 20 also includes osmotic member 21, as presented above. Capsule 20 of FIG. 2C includes a movable piston 22. The movable piston 22 moves or slides in response to pressure generated inside capsule 20. The piston is positioned between and in contacting relation with the active agent composition 19 and osmotic member 21. The piston serves to reduce diffusion and/or migration between the active agent composition and the osmotic member, thereby maintaining the concentration of the active agent composition. In addition, the piston prevents interaction between the active agent composition and the osmotic member 21.

Osmotic capsule 10 in operation imbibes fluid through wall 12 causing osmotic member 21 to expand and apply pressure against piston 22. This applied pressure moves piston 22 towards passageway 13 whereby the active agent composition 19 present in internal space 14 is pushed through passageway 13 into the environment of use. Examples of materials for manufacturing movable piston 22 include a member selected from the group consisting of a wax, petroleum wax, an ester of a high molecular weight fatty acid with a high molecular weight alcohol, a piston formed of an olefin polymer, a condensation polymer, rubber, organosilicon, high density polyethylene, high density polypropylene, and piston forming materials impermeable to fluid.

FIG. 2D illustrates another osmotic capsule 10 configuration of interest. In FIG. 2D, osmotic capsule 10 includes lead end 9, trailing end 8, capsule cap 17, active agent composition 19 in capsule body 16, osmotic member 21 in capsule body 16 closed by capsule cap 17. The components comprising FIG. 2D are as described above. In FIG. 2D, osmotic capsule 10 comprises wall 12 made from an injection-moldable composition by an injection-molding techniques. Injection-moldable compositions provided for injection-molding into wall 12 comprise a thermoplastic polymer, or the compositions comprise a mixture of thermoplastic polymers and optional injection-molding ingredients. The thermoplastic polymers that can be used for the present purpose comprise polymers that have a low softening point, for example, below 200° C., such as within the range of 40° C. to 180° C. The polymers may be synthetic resins, for example, linear polycondensation resins, condensation polymerized resins, addition polymerized resins, such as polyamides, resins obtained from diepoxides and primary alkanolamines, resins of glycerine and phthalic anhydrides, polymethane, polyvinyl resins, polymer resins with end-positions free or esterified carboxyl or carboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, and a resin composition comprising polycaprolactone, a polyalkylene oxide such as polyethylene oxide, poly(cellulose) such as poly((hydroxypropylmethylcellulose), poly(hydroxyethylmethylcellulose), poly(hydroxyethylcellulose), and poly(hydroxypropylkcellulose). The membrane forming composition can comprises optical membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another aspect comprises 10% to 99% of a thermoplastic polymer and 1% to 70% of a different polymer with the total equal to 100%. Also of interest is a thermoplastic polymer composition comprising 1% to 98% of a first thermoplastic polymer, 1% to 90% of a different, second polymer and 1% to 90% of a different, third polymer with all polymers equal to 100%. Compositions of interest include a composition of 20% to 90% of thermoplastic polycaprolactone and 10% to 80% of poly(alkylene oxide); a composition comprising 20% to 90% of poly(alkylene oxide); a composition comprising 20% to 90% polycaprolactone and 10% to 60% of poly(ethylene oxide) with the ingredients equal to 100%; a composition comprising of 10% to 97% polycaprolactone, 10% to 97% poly(alkylene oxide), and 1% to 97% of poly(ethylene glycol) with all ingredients equal to 100%; a composition comprising 20% to 90% polycaprolactone and 10% to 80% of polyethylene glycol 40 stearate, with all ingredients equal to 100%; and a composition comprising 1% to 90% polycaprolactone, 1% to 90% poly(ethylene oxide), 1% to 90% poly (hydroxypropylcellulose) and 1% to 90% poly(ethylene glycol) with all ingredients equal to 100%. The percent, expressed is weight percent, wt %.

Figure 3:
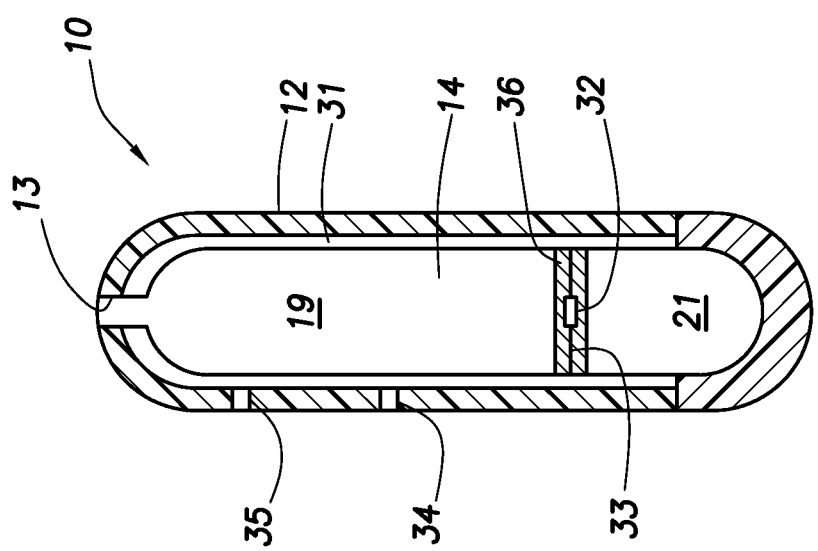
FIG. 3 provides a view of an ingestible event marker associated with an osmotic component of an osmotic capsule.

The expression "passageway" as used herein refers to a structure 13 useful for delivery of active agent from the interior of the osmotic capsule to the outside environment of the osmotic capsule. The expression includes passage way, aperture, hole, bore, pore and the like through the semipermeable wall 12. The passageway can be formed by mechanical drilling, laser drilling, or by eroding an erodible element, such as a gelatin plug, salt plug, a pressed glucose plug, to yield the orifice, when the dosage form is in the environment of use. In an aspect, the orifice in wall 12 is formed in the environment of use in response to the hydrostatic pressure generated in osmotic capsule 10. In another aspect, the osmotic capsule 10 can be manufactured with two or more orifices in spaced-class relation for delivering active agent 19. The passageway 13 can be formed by mechanical rupturing of wall 12.

Where the ingestible component is an osmotic capsule, the IEM may be stably associated with a variety of different components of the osmotic capsule, as desired. In some instances, the IEM may be associated with the osmotic member in some manner. For example, the IEM may be positioned within the osmotic member. Alternatively, the IEM may be associated with or completely replace the piston 22 shown in FIG. 2C. An example of such as osmotic capsule is shown in FIG. 3. In FIG. 3, osmotic capsule 10 includes hard-capsule component 31, which may be made from any convenient material, such as hydroxypropylmethylcellulose (HPMC). Hard-capsule component 31 is configured with as a partial capsule in the aspect shown in FIG. 3, and together with semipermeable wall 12 defines an inner space 14. Also shown is osmotic member 21. In the aspect shown in FIG. 3, IEM 32 is configured as a barrier that separates the osmotic member 21 and the active agent composition 19. Where the IEM 32 serves as a barrier separating the osmotic member 21 from the active agent composition 19, the IEM membrane 33 may be dimensioned to conform to the inner walls of the hard-capsule component 31 and therefore serve as the barrier. Where the IEM is present inside the capsule, the hard-capsule component 31 may include, e.g., form, one or more holes 34 and 35 positioned at various locations to enhance communication from the IEM to the outside of the capsule, e.g., via conductive transmission. These one or more holes may be positioned at any convenient location in the wall. Optionally, the IEM 32 may be associated with a micro-environment member 36 which controls the micro-environment of the IEM. For example, micro-environment member 36 may be a dried conductive medium layer (for example a salt layer) that surrounds the IEM 32, and upon wetting provides for a defined conductive medium environment for the IEM. Details regarding micro-environment members and materials that may be employed for the same are further provided in PCT application serial no. PCT/US2007/082563 published as WO 2008/052136; the disclosure of which is herein incorporated by reference. In fabricating the osmotic capsule shown in FIG. 3, the capsule structure may be first produced using any convenient protocol and then filled with the active agent composition, e.g., by introducing the active agent composition into internal space 14 through passageway 13. As indicated above, the active agent layer may be a liquid or solid, such as a powder. In those instances where the active agent composition is a solid, such as a powder, a layered active agent composition may be positioned in the capsule, with two or more layers of differing active agent compositions, as desired. In other instances, the hard-capsule component may be filled with the active agent composition and sealed with the osmotic member 21. The resultant structure may then be encased in the semipermeable wall 12 and the passageway 13 produced, for example by laser drilling.

Figure 4:
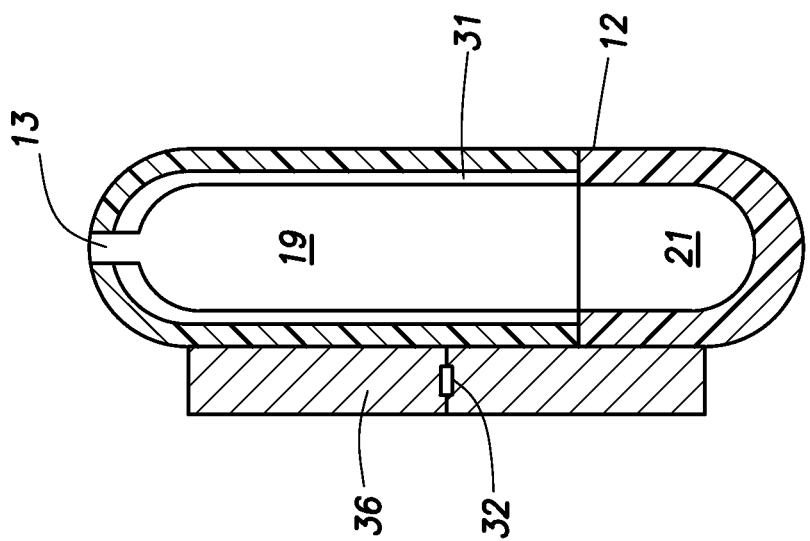
FIG. 4 provides a view of an ingestible event marker associated with the outer surface an osmotic capsule.

Instead of being present inside of the capsule, the IEM may be stably associated with an outer location of the capsule. An example of such a configuration is shown in FIG. 4. In FIG. 4, osmotic capsule 10 includes hard capsule component 31, osmotic member 21, semipermeable wall 12, passageway 13 and active agent composition 19, as described above. Also shown is IEM 32 stably associated with the outer surface of the capsule. IEM 32 is present in a micro-environment member 36, as described above. The IEM 32 and micro-environment member 36 may be adhered to wall 12 using any convenient protocol, such as via a suitable physiologically acceptable adhesive material. Where desired, a wetting agent (not shown) may be associated with the micro-environment member 36, such as between the micro-environment member 36 and wall 12, so as to assure uniform wetting of the micro-environment member 36.

Instead of including a single IEM, osmotic capsules may include multiple IEMs stably and/or freely associated with different locations of the capsule. An example of such an osmotic capsule is shown in FIG. 5. In FIG. 5, osmotic capsule 10 includes hard-capsule component 31, osmotic member 21, semipermeable wall 12, passageway 13 and active agent composition 19, as described above. In addition, osmotic capsule 10 includes piston 22, as described above. Also shown are three different IEMs, 51, 52 and 53, which are integrated with different regions of the wall 12. Where desired, IEMs 51, 52 and 53 may include membranes which are co-manufactured with the wall 12. While IEMs 51, 52 and 53 are integrated with different regions of the wall 12, in some instances the multiple IEMs may be adhered to different surface locations of the outer surface of wall 12, for example in analogous fashion to that depicted in FIG. 4. Where desired, the IEMs 51, 52 and 53 may be configured to emit a signal only when the osmotic member 21 is level with the IEM. For example, as shown in FIG. 5, as osmotic member 21 imbibes fluid, piston 22 moves in the direction of the arrow. IEMs 51, 52 and 53 only activate and emit a signal when piston 22 passes the IEM and the osmotic member 21 becomes level with the IEM. As such, the osmotic capsule of this aspect is configured such that each IEM emits a signal when it is level with the osmotic member. This controlled activation may be achieved using any convenient protocol, such as by including a necessary chemical reagent for IEM activation in the osmotic member 21. Such aspects provide for the ability to monitor delivery parameters of the osmotic capsule by evaluating the timing of signals received from the IEMs 51, 52 and 53. For example, by recording the timing of receipt of the signal from IEMs 51, 52 and 53, the rate of movement of piston 22 and therefore delivery of active agent from the osmotic capsule 10 may be readily determined.

As indicated above, one or more IEMs may be associated with a variety of different locations of an osmotic capsule. Examples of locations of an osmotic capsule where IEMs may be positioned include, but are not limited to, those locations depicted in FIG. 6. In FIG. 6, potential IEM locations 61, 62, 63, 64 and 65 are shown. A given osmotic capsule may include a single IEM at only one of these locations, or two or more IEMs at any two or more of these locations. Depending on the location, the IEM may be integrated with different components of the osmotic capsule and/or attached to the osmotic capsule component. Where the IEM is integrated with a given component (for example, the piston, a passageway plug, a capsule component, a semipermeable wall, etc.,) it may be co-manufactured with that component, as desired.

Liquid Capsule Ingestible Component

Another type of ingestible component of interest is a liquid capsule. Liquid capsules are ingestible components that include a shell (such as an outer capsule) filled with a liquid medium. The shell, for example outer capsule, may be a single component structure or a two-component structure, e.g., as described above in connection with osmotic capsule aspects, above. The liquid medium present inside of the shell may vary greatly, and may or may not include an active agent. While the shell may have a variety of configuration so long as it is configured to hold a desired amount of liquid medium (such as a liquid active agent composition), in certain aspects of interest the shell has a capsule configuration. As such, for ease of description only the shell will now be further described in terms of capsule configurations.

IEMs may include one or more IEMs stably associated in some manner with the liquid capsule. The IEM may be stably associated with the liquid capsule in a variety of different ways. In some instances, the IEM is located in the liquid medium of the liquid capsule. In such instances, the IEM may be protected in some manner from the liquid medium. For example, the IEM may be coated with a coating that protects the IEM from the liquid medium.

When present, such as coating may cover one or more surfaces of the IEM or all of the surfaces of the IEM, such that the IEM is enveloped by the coating. Coatings of interest include pliable as well as non-pliable coatings. Coatings may take a variety of different configurations, such as layers, snap-fit pre-made structures, etc. When present, coatings may cover only a portion of the IEM or envelope the entire IEM. The coating may be uniform or non-uniform in terms of thickness.

Figure 8:
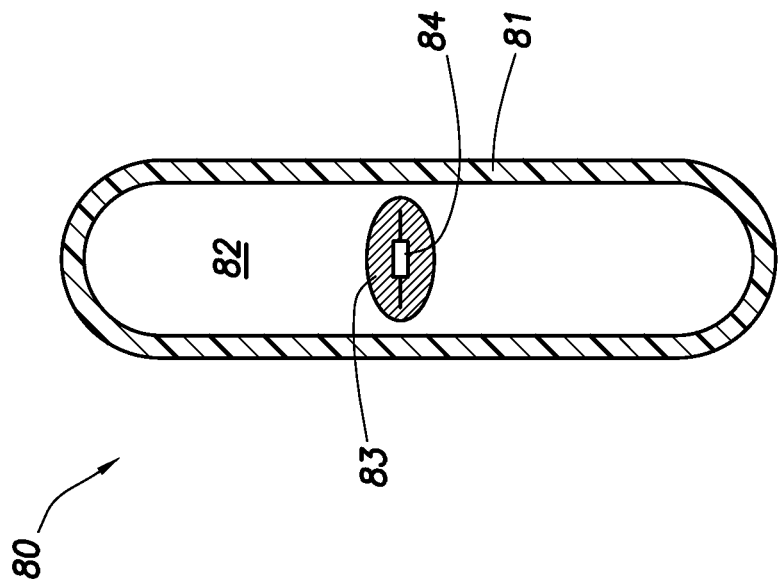
FIG. 8 provides a view of a vesicle-encased ingestible event marker is present inside of a liquid capsule.
Figure 7:
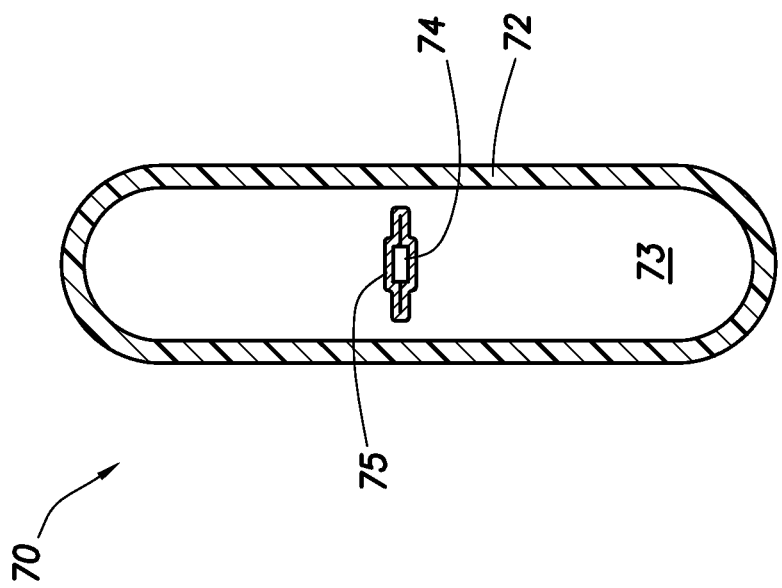
FIG. 7 provides a view of a coated ingestible event marker present inside of a liquid capsule.

In certain instances, the coating is a pH sensitive coating covering various components of the IEM, where the pH sensitive coating only dissolves to expose the components when the desired pH conditions are present. pH sensitive coatings of interest include, but are not limited to: cellulose acetate pthalate, EUDRAGIT L™, EUDRAGIT S™, EUDRAGIT FS™, and other pthalate salts of cellulose derivatives. FIG. 7 provides a view of a configuration 70 that includes an outer capsule 72 containing a liquid medium 73, which liquid medium may contain an active agent. Present inside of outer capsule 72 is IEM 74. IEM 74 is coated with a pH sensitive coating 75. The pH sensitive coating may be chosen such that it remains intact in the liquid medium (for example where a low pH is present) but readily dissolves at higher pHs, such as the pH environment of the gastrointestinal tract.

Where desired, the IEM (optionally coated with a protective layer, such as described above) that is located in the liquid medium may be present inside of a vesicle. The term "vesicle" is employed in its conventional sense to reference to a fluid filled compliant structure. For example, the IEM may be present inside of a lipid vesicle, e.g., where the liquid medium is an aqueous medium. FIG. 8 provides an example of an IEM according to this aspect. In FIG. 8, IEM 80 includes outer capsule 81 containing aqueous liquid medium 82. Present in aqueous liquid medium 82 is vesicle 83, where IEM 84 is present in the vesicle 83. The vesicle may be fabricated from any convenient material, such as lipids etc., where the choice of material may depend, at least in part, on the nature of the liquid medium, e.g., whether it is aqueous or non-aqueous, polar or non-polar, etc.

Figure 9:
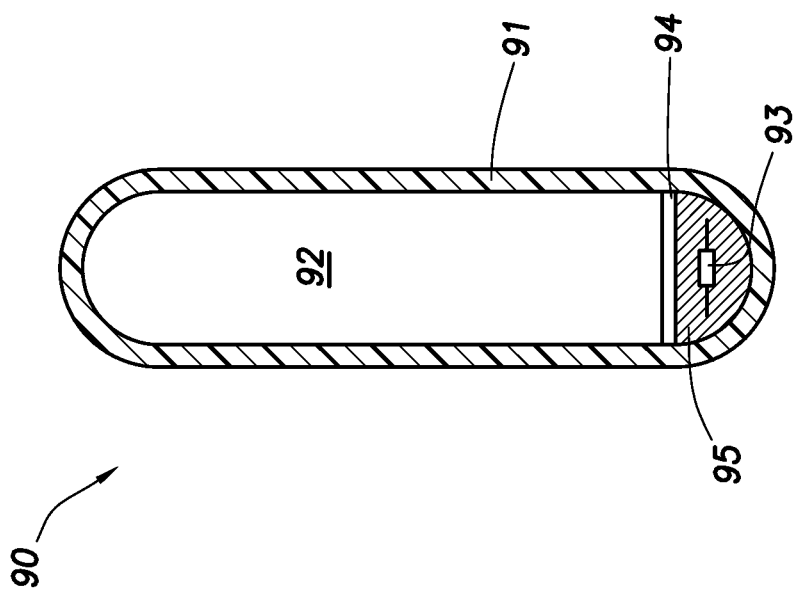
FIG. 9 provides a view of an ingestible event marker present inside of a sealed compartment inside of a liquid capsule.

Instead of a vesicle, the IEM may be present in an encasing liquid that is immiscible with the liquid medium. For example, where the liquid medium is an aqueous liquid, the IEM may be present in a volume of a non-polar organic liquid that is immiscible in the aqueous liquid medium. As such, the IEM remains inside of the volume of immiscible encasing liquid when present in the liquid medium of the capsule.

Where desired, the IEM may be present in a sealed compartment inside of the outer capsule. FIG. 9 shows IEM 90 that includes outer capsule 91 and liquid medium 92. Barrier 94, in conjunction with capsule 91, defines an internal sealed compartment 95. Present inside of sealed compartment 95 is IEM 93.

Figure 10A:
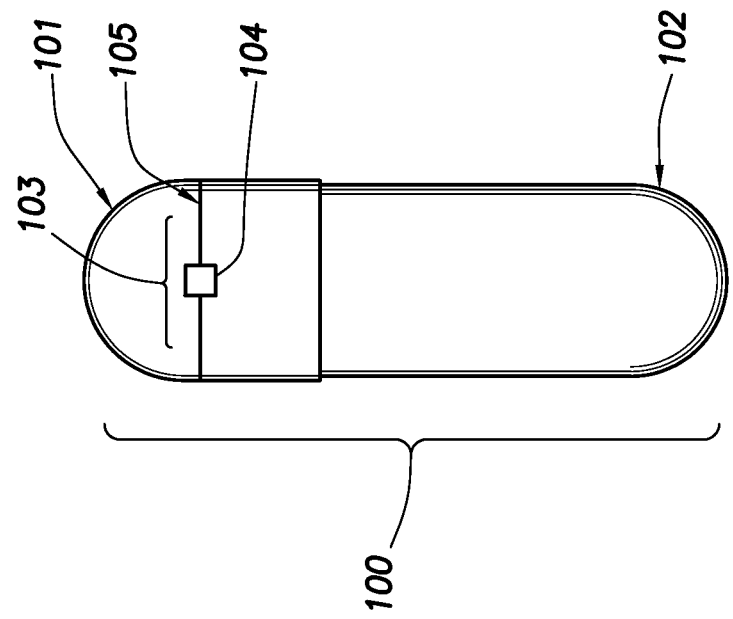
FIGS. 10A to 10B illustrate a liquid capsule (as well as a method for its fabrication) in which an ingestible event marker is integrated with a capsule component of the liquid capsule.
Figure 10B:
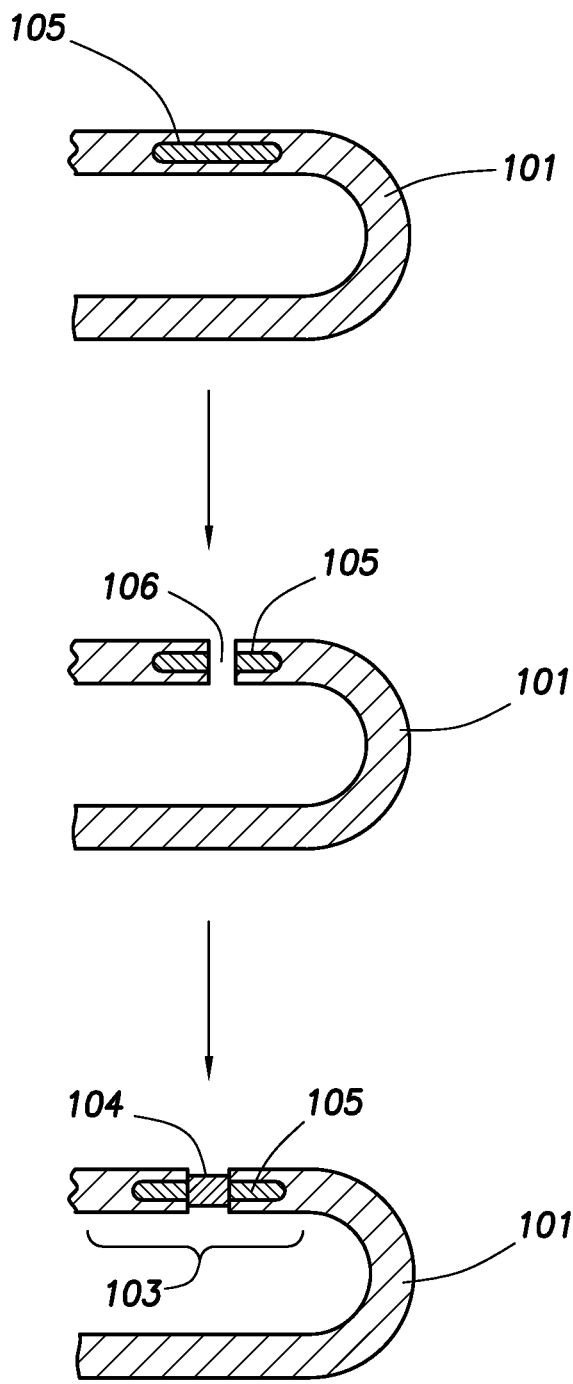

In some instances, the IEM is integrated with the outer capsule. As the IEM is integrated with the outer capsule, in some aspects, the IEM cannot be removed from the remainder of the outer capsule without significantly compromising the structure and functionality of the outer capsule. In FIG. 10A, IEM 100 includes capsule cap 101 and capsule body 102. In capsule cap 101, IEM 103 is present, which is made up of IC component 104 and membrane 105. FIG. 10B provides an illustration of one protocol for fabricating the configuration shown in FIG. 10A. In the aspect illustrated in FIG. 10B, membrane 105 is provided in prefabricated capsule cap 101. Next, a hole 106 is provided in membrane 105, e.g., via punching or laser drilling. Following this step, IC component 104 is placed in hole 106 to produce IEM 103, where the IC component 104 may be held in place with an adhesive, as desired. FIG. 10A provides an illustration of an aspect where the membrane is integral with the capsule component of capsule IEM 100. In yet other aspects, the capsule component and the membrane may be the same structure. In those aspects where the IEM is integrated with the capsule, the IEM may be integrated at a variety of different locations, as desired. Accordingly, the IEM may be integrated in the capsule at one of the poles, at a side location, etc.

IEM Attachment Via Mechanical Stable Association

Ingestible event markers of the invention may include an ingestible component and one or more IEMs that are mechanically stably associated with the ingestible component. In these instances, the IEMs include an IEM that is mechanically stably associated with the ingestible component. By "mechanically stably associated" is meant that the stable association is provided by some mechanical component, such as a snap-fit component, etc. As such, the stable association is provided by non-chemical interaction, such as by friction or other physical forces. In IEMs of these aspects, the ingestible component may have any of a variety of different configurations, such as tablets, capsules, etc.

Figure 11:
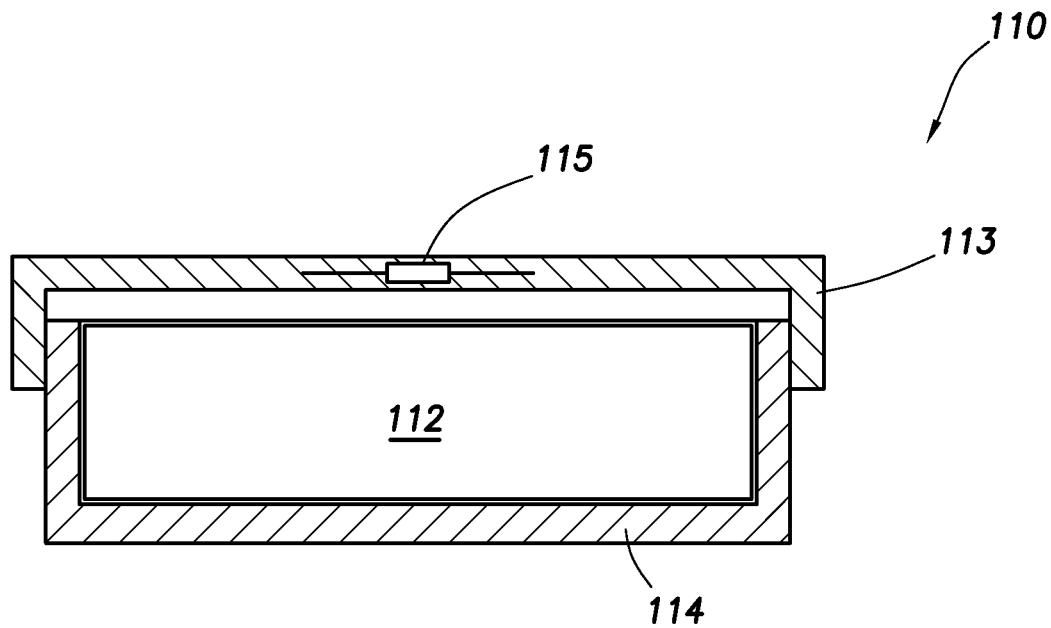
FIG. 11 provides a view of an ingestible event marker integrated into a lid that associates with a container to encase a tablet.

In some instances, the IEM has a structure in which the ingestible component is present in an encasement that comprises the IEM, for example whether the IEM is integrated with the encasement or a component thereof. The encasement of such aspects may have any convenient configuration, so long as it encases the ingestible component. For example, the encasement may include a lid and a container configured to associate with each other in a manner sufficient to encase the ingestible component. An example of such an IEM is shown in FIG. 11. In FIG. 11, IEM 110 includes ingestible component 112 in the form of a tablet. Tablet 112 is present inside of container 114. Also shown is lid 113 which is associated with container 114 to encase tablet 112. Lid 113 includes integrated IEM 115. The association of lid 113 and container 114 may vary, so long as the association is stable and provides for the encasement of tablet 112. For example, lid 113 may be stably associated with container 114 with an adhesive. In such instances, while lid 113 is associated with container 114 by an adhesive, the tablet 112 is maintained in the encasement structure merely be physical entrapment in the encasement structure, so as to minimize any modification to the tablet 112. Instead of an adhesive, the lid and container may be configured to have a snap-fit relationship with each other, such that the lid and container are configured to snap-fit together. In such instances, pressure is applied to the lid and/or container to associate the two structures with each other. Once associated, the pressure may be removed and the two components will remain stably associated with each other.

Figure 12:
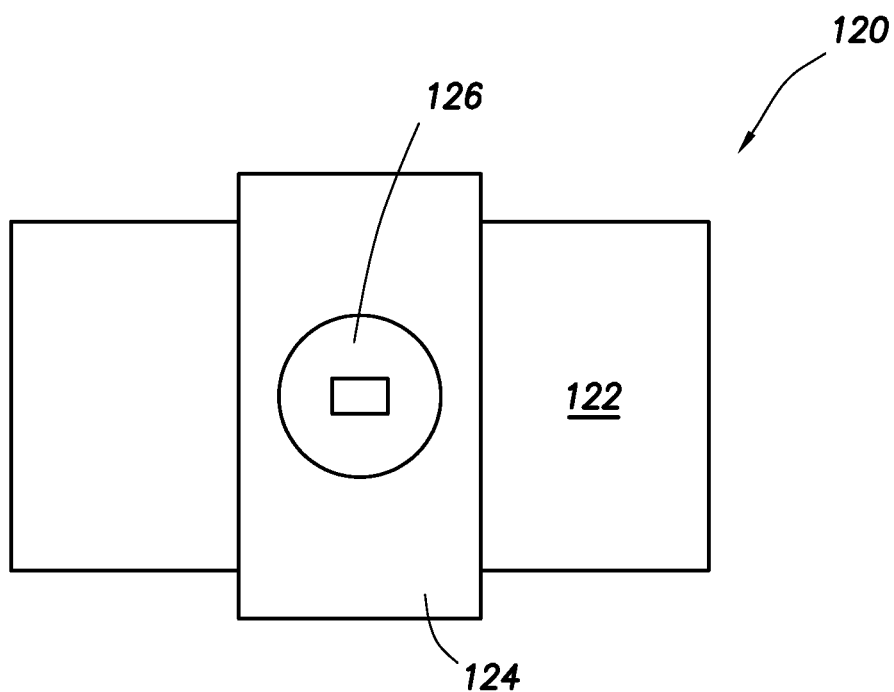
FIG. 12 provides a view of an ingestible event marker integrated into a non-encasing band that associates with a tablet.

Instead of being associated with an encasement, the IEM may include a non-encasing component that is configured to mechanically stably associate with the ingestible component, where the non-encasing component comprises the IEM. As this IEM comprising component is non-encasing, upon association with the ingestible component, it covers a portion of the surface of the ingestible component but not the entire surface of the ingestible component. Non-encasing components of interest may have a variety of different configurations, such as bands, clips, cuffs, sleeves, clamps, claws, etc. The non-encasing component may be fabricated from any convenient material, where materials of interest include physiologically acceptable elastomeric materials that are compatible with a given IEM that is to be employed. An example of an IEM that includes a non-encasing component is illustrated in FIG. 12. In FIG. 12, IEM 120 includes ingestible component 122 in the form of a tablet. Band 124 is fabricated from an elastomeric material and is configured to fit over and securely associate with the tablet 122 as shown. Integrated into band 124 is IEM 126, as shown.

Instead of being integrated in a band or analogous structure, such as shown in FIG. 12, the IEM may be separate from the non-encasing component and yet stably associated with the ingestible component by the non-encasing component. In such instances, the non-encasing component may be configured to change conformation upon contact of the IEM with the target site so as to separate the IEM from the ingestible component. For example, the non-encasing component may have a configuration and be fabricated from a material such that, upon contact with a target site, the non-encasing component or a portion thereof swells (for example, upon absorption of water) such that the non-encasing component changes shape and is released from the ingestible component. Upon release from the ingestible component, the non-encasing component releases one or IEMs that were stably associated with the ingestible component by the non-encasing component, for example where the IEMs were present between the ingestible component and the non-encasing component. In these aspects, the non-encasing component may be shaped in a variety of different ways, such as band-shaped, star-shaped, daisy-shaped, etc. The non-encasing component may be fabricated from a variety of different types of materials, where materials of interest include polymeric materials, such as described above.

Figure 13A:
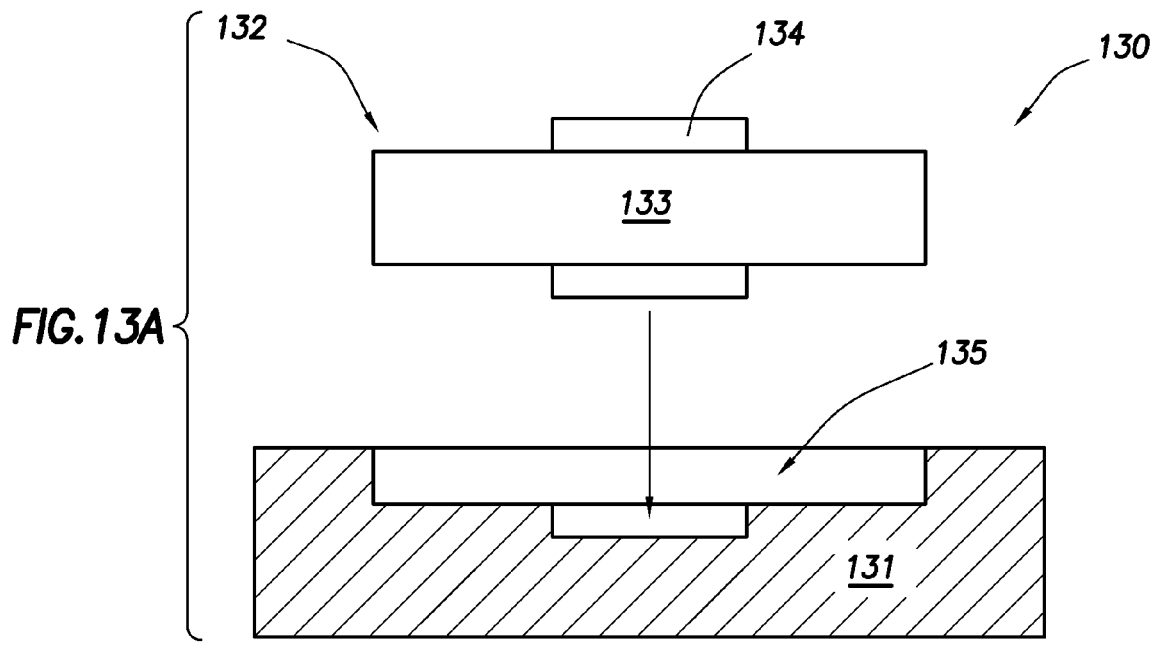
FIGS. 13A and 13B provide a view of an ingestible event marker where an identifier is press-fit into a receiving element of a tablet.
Figure 13B:
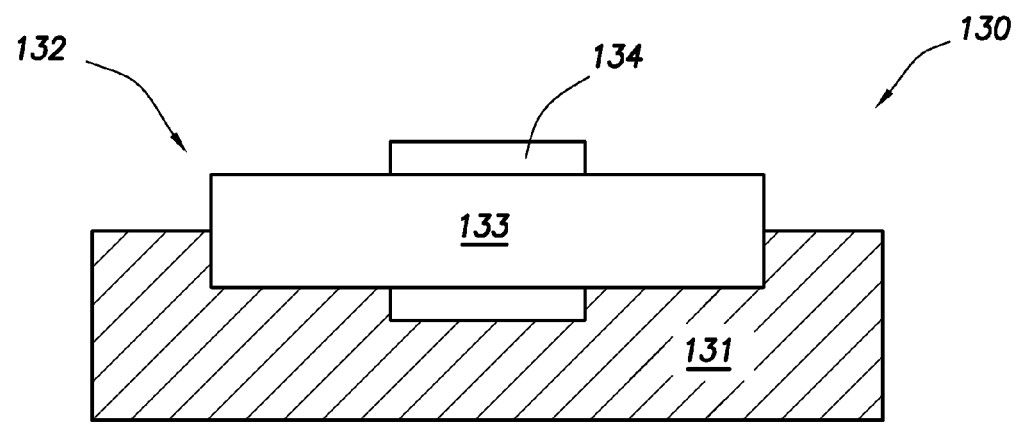

In some instances, the ingestible component includes an IEM receiving element configured to receive the IEM, where the IEM is configured to be retained in the receiving element following placement therein by mechanical forces. The receiving element may vary in terms of configuration. Examples of receiving element configurations include grooves, cup-shapes, or more complex structures, where the configuration may depend, at least in part, on the configuration of the IEM that is to be mechanically stably associated in the receiving element. For example, the IEM may be configured to press-fit into the receiving element. As such, once the IEM is positioned in the receiving element, the IEM is maintained in the receiving element without any additional applied force and/or chemical adhesives. To provide for this relationship, the IEM may include a flexible component that conforms to the receiving element upon placement of the IEM into the receiving element. The flexible component may be any component of the IEM. In some instances, the flexible component may be a membrane of the IEM. An example of an IEM as described above is shown in FIGS. 13A and 13B. FIG. 13A provides a view of IEM 130 prior to assembly. IEM 130 includes ingestible component 131 in the form of a tablet. Tablet 131 includes IEM receiving element 135 that is configured and dimensioned to receive IEM 132. IEM 132 includes IC component 134 and flexible membrane 133. To assemble IEM 130, IEM 132 is positioned in receiving element 135 as shown by the arrow in FIG. 13A to produce the assembled IEM 130 shown in FIG. 13B. The diameter of flexible membrane 133 is slightly larger than the diameter of receiving element 135. As such, the IEM 132 may be pressed into the receiving element 131, but will then stay in position in the receiving element following removal of any pressing force.

Where desired, the flexible component (such as the membrane or another structure) may be configured to be folded during placement into the receiving element. In such configurations, following placement of the IEM in the receiving element, the folded flexible component may be allowed to unfold to secure the IEM in the receiving element. The flexible component of such IEMs may have a variety of different configurations that are amenable to manipulation (such as folding) to provide for insertion into the receiving element, as described above. Configurations of interest include both simple configurations, such as disc-shaped configurations, or more complex configurations, such as star-shaped configurations.

In some instances, the IEM may include a feature that mates with one a feature of the ingestible component. For example, the IEM may include a hole, for example in a membrane, which receives a corresponding protrusion, such as a peg, of the ingestible component. When the protrusion is placed through the hole, the IEM becomes stably associated with the ingestible component. These mating features may be configured to have a snap-fit relationship, e.g., as described above.

Multi-Layered Ingestible Components

Another type of ingestible component of interest is a multi-layered ingestible component, where the ingestible component includes two or more distinct layers of material. Multi-layered ingestible components are not homogenous ingestible components, in which there is no variation throughout the ingestible component in terms of composition. Multi-layered ingestible components may be include only two distinct layers, more than two layers, such as three, four, five, ten, fifteen or even twenty layers or more. The different layers may or may not be separated from each other by a barrier material, as desired. Each layer may have the same or different composition. In some instances, the different layers may have the same active agent in the same concentration. Alternatively, the different layers may have the same active agent but in differing concentrations. In yet other aspects, two or more different active agents may be present in two or more different layers. As with the active agents, the vehicle component of the layers may be the same or different, as desired, e.g., to provide for desired controlled release profiles, and the like.

Associated with one or more of the layers the multi-layered ingestible component is one or more IEMs. An IEM may be present in only one, some or all of the layers of a multi-layered ingestible component. In some instances, the layer or layers in which an IEM is present are layers that do not include an active agent. Alternatively, IEM-containing layers may also contain an active agent. Where multiple layers include IEMs, the IEMs may activate at different times and/or locations of the GI tract to provide information regarding when an active agent was released from the ingestible component. In multi-layered ingestible components where the IEM layers alternate with active agent layers, the ingestible component may be configured such that active agent from a given layer is only released following activation of an IEM in the layer above that active agent layer. Multi-IEM multi-layered ingestible components may be configured such that different IEMs send different signals (for example that differ from each other in terms of ID), so that dissolution of each layer of the multi-layered ingestible component may be detected and/or monitored, as desired.

The multi-layered ingestible component may or may not include non-multi-layered elements. For example, multi-layered ingestible components of interest include multi-layered tablets. Also of interest are capsules that have multiple layers present inside an outer shell component. Also of interest are tablets and capsules that have a distinct multi-layer component, e.g., as described above, stably associated with non-multi-layered tablet or capsule. For example, the IEM may include a multilayered membrane. All such formats are considered multi-layered ingestible components because they include a multi-layer element, e.g., as described above.

The ingestible component may also be configured so that the IEM can activate in a manner that is independent of any controlled release profile of the remainder of the ingestible component. For example, the IEM may be present in a first layer configured so that the IEM present therein is activated upon contact with a desired physiological site, such as the stomach or small intestine. In these aspects, the ingestible component may include a second layer that is configured to provide for controlled release of an active agent.

Multi-Compartment Ingestible Components

Also of interest as ingestible components are multi-compartment ingestible components. Multi-compartment ingestible components are ingestible components that include two or more distinct compartments or regions that are distinct from other in terms of one or more parameters, such as dissolution profile, composition, etc. In such ingestible components, an IEM is associated with at least one of the compartments. Multi-compartment ingestible components may be configured to separate the one or more IEMs from the remainder of the ingestible component to provide for one or more desired characteristics. For example, the IEM may be positioned in a compartment distinct from the remainder of the ingestible component in order to protect the IEM from other constituents of the ingestible component, such as the active agent, from moisture, e.g., as may be present in a liquid containing ingestible component, etc.; also, stability, e.g., to provide for stability of the IEM and components thereof. Alternatively, the multi-compartment ingestible component may be configured to provide for a desired environment for the IEM when active, e.g., by providing a controlled ion concentration, such as described in application serial no. PCT/US2007/082563 published as WO 2008/052136 the disclosure of which is herein incorporated by reference, and/or controlled activation, e.g., in response to a predetermined environmental condition, such as pH.

The ingestible component may also be configured so that the IEM can activate in a manner that is independent of any controlled release profile of the remainder of the ingestible component. For example, the IEM may be present in a first compartment configured so that the IEM present therein is activated upon contact with a desired physiological site, such as the stomach or small intestine. In these aspects, the ingestible component may include a second compartment that is configured to provide for controlled release of an active agent.

Also of interest ingestible components that include a controlled release compartment, where the controlled release compartment includes an IEM. In such ingestible components, the IEM may be activated at with release of the active agent from the controlled release compartment begins, such that an IEM communication may be used to determine the onset of active agent delivery from the controlled release compartment.

Active Agent

Where desired, the IEM and/or ingestible component may include an active agent. The active agent, when present, may be present in the IEM, ingestible component, the membrane, or both. Active agents of interest include pharmaceutically active agents as well as non-pharmaceutical active agents, such as diagnostic agents.

The phrase "pharmaceutically active agent" (also referred to herein as drugs) refers to a compound or mixture of compounds which produces a physiological result, e.g., a beneficial or useful result, upon contact with a living organism, e.g., a mammal, such as a human. Pharmaceutically active agents are distinguishable from such components as excipients, carriers, diluents, lubricants, binders and other formulating aids, and encapsulating or otherwise protective components. The pharmaceutically active agent may be any molecule, as well as binding portion or fragment thereof, that is capable of modulating a biological process in a living subject. In certain aspects, the pharmaceutically active agent may be a substance used in the diagnosis, treatment, or prevention of a disease or as a component of a medication. In certain aspects, the pharmaceutically active agent may be a chemical substance, such as a narcotic or hallucinogen, which affects the central nervous system and causes changes in behavior. The pharmaceutically active agent is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The pharmaceutically active agent may include one or more functional groups necessary for structural interaction with the target, e.g., groups necessary for hydrophobic, hydrophilic, electrostatic or even covalent interactions, depending on the particular drug and its intended target. Where the target is a protein, the pharmaceutically active agent may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Pharmaceutically active agents of interest may include cyclical carbon or heterocyclic structures and/or aromatic or polyaromatic structures substituted with one or more of the above functional groups. Also of interest as pharmaceutically active agents are compounds having structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The pharmaceutically active agent may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the pharmaceutically active agent may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., antineoplastic) agents; neurological agents, e.g., anti-convulsants, etc.

In certain aspects, the active agent is a cardiovascular agent, i.e., an agent employed in the treatment of cardiovascular or heart conditions. In certain aspects, the active agent is a cardiovascular agent, i.e., an agent employed in the treatment of cardiovascular or heart conditions. Cardiovascular agents of interest include, but are not limited to: cardioprotective agents, e.g., Zinecard (dexrazoxane); blood modifiers, including anticoagulants (e.g., coumadin (warfarin sodium), fragmin (dalteparin sodium), heparin, innohep (tinzaparin sodium), lovenox (enoxaparin sodium), orgaran (danaparoid sodium)) antiplatelet agents (e.g., aggrasta (tirofiban hydrochloride), aggrenox (aspirin/extended release dipyridamole), agrylin (anagrelide hydrochloride), ecotrin (acetylsalicylic acid), folan (epoprostenol sodium), halfprin (enteric coated aspirin), integrlilin (eptifibatide), persantine (dipyridamole USP), plavix (clopidogrel bisulfate), pletal (cilostazol), reopro (abciximab), ticlid (ticlopidine hydrochloride)), thrombolytic agents (activase (alteplase), retavase (reteplase), streptase (streptokinase)); adrenergic blockers, such as cardura (doxazosin mesylate), dibenzyline (phenoxybenzamine hydrochloride), hytrin (terazosin hydrochloride), minipress (prazosin hydrochloride), minizide (prazosin hydrochloride/polythiazide); adrenergic stimulants, such as aldoclor (methyldopa—chlorothiazide), aldomet (methyldopa, methyldopate HCl), aldoril (methyldopa—hydrochlorothiazide), catapres (clonidine hydrochloride USP, clonidine), clorpres (clonidine hydrochloride and chlorthalidone), combipres (clonidine hydrochloride/chlorthalidone), tenex (guanfacine hydrochloride); alpha/bet adrenergic blockers, such as coreg (carvedilol), normodyne (labetalol hydrochloride); angiotensin converting enzyme (ACE) inhibitors, such as accupril (quinapril hydrochloride), aceon (perindopril erbumine), altace (ramipril), captopril, lotensin (benazepril hydrochloride), mavik (trandolapril), monopril (fosinopril sodium tablets), prinivil (lisinopril), univasc (moexipril hydrochloride), vasotec (enalaprilat, enalapril maleate), zestril (lisinopril); angiotensin converting enzyme (ACE) inhibitors with calcium channel blockers, such as lexxel (enalapril maleate—felodipine ER), lotrel (amlodipine and benazepril hydrochloride), tarka (trandolapril/verapamil hydrochloride ER); angiotensin converting enzyme (ACE) inhibitors with diuretics, such as accuretic (quinapril HCl/hydroclorothiazide), lotensin (benazepril hydrochloride and hydrochlorothiazide USP), prinizide (lisinopril—hydrochlorothiazide), uniretic (moexipril hydrochloride/hydrochlorothiazide), vaseretic (enalapril maleate—hydrochlorothiazide), zestoretic (lisinopril and hydrochlorothiazide); angiotensin II receptor antagonists, such as atacand (candesartan cilexetil), avapro (irbesartan), cozaar (losartan potassium), diovan (valsartan), micardis (telmisartan), teveten (eprosartan mesylate); angiotensin II receptor antagonists with diuretics, such as avalide (irbesartan—hydrochlorothiazide), diovan (valsartan and hydrochlorothiazide), hyzaar (losartan potassium—hydrochlorothiazide); antiarrhythmics, such as Group I (e.g., mexitil (mexiletine hydrochloride, USP), norpace (disopyramide phosphate), procanbid (procainamide hydrochloride), quinaglute (quinidine gluconate), quinidex (quinidine sulfate), quinidine (quinidine gluconate injection, USP), rythmol (propafenone hydrochloride), tambocor (flecainide acetate), tonocard (tocainide HCl)), Group II (e.g., betapace (sotalol HCl), brevibloc (esmolol hydrochloride), inderal (propranolol hydrochloride), sectral (acebutolol hydrochloride)), Group III (e.g., betapace (sotalol HCl), cordarone (amiodarone hydrochloride), corvert (ibutilide fumarate injection), pacerone (amiodarone HCl), tikosyn (dofetilide)), Group IV (e.g., calan (verapamil hydrochloride), cardizem (diltiazem HCl), as well as adenocard (adenosine), lanoxicaps (digoxin), lanoxin (digoxin)); antilipemic acids, including bile acid sequestrants (e.g., colestid (micronized colestipol hydrochloride), welchol (colesevelam hydrochloride)), fibric acid derivatives (e.g., atromid (clofibrate), lopid (gemfibrozal tablets, USP), tricor (fenofibrate capsules)), HMG-CoA reductase inhibitors (e.g., baycol (cerivastatin sodium tablets), lescol (fluvastatin sodium), lipitor (atorvastatin calcium), mevacor (lovastatin), pravachol (pravastatin sodium), zocor (simvastatin)), Nicotinic Acid (e.g., Niaspan (niacin extended release tablets)); beta adrenergic blocking agents, e.g., betapace (sotalol HCl), blocadren (timolol maleate), brevibloc (esmolol hydrochloride), cartrol (carteolol hydrochloride), inderal (propranolol hydrochloride), kerlone (betaxolol hydrochloride), nadolol, sectral (acebutolol hydrochloride), tenormin (atenolol), toprol (metoprolol succinate), zebeta (bisoprolol fumarate); beta adrenergic blocking agents with diuretics, e.g., corzide (nadolol and bendroflumethiazide tablets), inderide (propranolol hydrochloride and hydroclorothiazide), tenoretic (atenolol and chlorthalidone), timolide (timolol maleate—hydrochlorothiazide), ziac (bisoprolol fumarate and hydrochlorothiazide); calcium channel blockers, e.g., adalat (nifedipine), calan (verapamil hydrochloride), cardene (nicardipine hydrochloride), cardizem (diltiazem HCl), covera (verapamil hydrochloride), isoptin (verapamil hydrochloride), nimotop (nimodipine), norvasc (amlodipine besylate), plendil (felodipine), procardia (nifedipine), sular (nisoldipine), tiazac (diltiazem hydrochloride), vascor (bepridil hydrochloride), verelan (verapamil hydrochloride); diuretics, including carbonic anhydrase inhibitors (e.g., daranide (dichlorphenamide)), combination diuretics (e.g., aldactazide (spironolactone with hydrochlorothiazide), dyazide (triamterene and hydrochlorothiazide), maxzide (triamterene and hydrochlorothiazide), moduretic (amiloride HCl—hydrochlorothiazide)), loop diuretics (demadex (torsemide), edecrin (ethacrynic acid, ethacrynate sodium), furosemide), potassium-sparing diuretics (aldactone (spironolactone), dyrenium (triamterene), midamor (amiloride HCl)), thiazides & related diuretics (e.g., diucardin (hydroflumethiazide), diuril (chlorothiazide, chlorothiazide sodium), enduron (methyclothiazide), hydrodiuril hydrochlorothiazide), indapamide, microzide (hydrochlorothiazide) mykrox (metolazone tablets), renese (polythi-azide), thalitone (chlorthalidone, USP), zaroxolyn (metolazone)); inotropic agents, e.g., digitek (digoxin), dobutrex (dobutamine), lanoxicaps (digoxin), lanoxin (digoxin), primacor (milrinone lactate); activase (alteplase recombinant); adrenaline chloride (epinephrine injection, USP); demser (metyrosine), inversine (mecamylamine HCl), reopro (abciximab), retavase (reteplase), streptase (streptokinase), tnkase (tenecteplase); vasodilators, including coronary vasodilators (e.g., imdur (isosorbide mononitrate), ismo (isosorbide mononitrate), isordil (isosorbide dinitrate), nitrodur (nitroglycerin), nitrolingual (nitroglycerin lingual spray), nitrostat (nitroglycerin tablets, USP), sorbitrate (isosorbide dinitrate)), peripheral vasodilators & combinations (e.g., corlopam (fenoldopam mesylate), fiolan (epoprostenol sodium), primacor (milrinone lactate)), vasopressors, e.g., aramine (metaraminol bitartrate), epipen (EpiPen 0.3 mg brand of epinephrine auto injector, EpiPen Jr. 0.15 mg brand of epinephrine auto injector), proamatine (midodrine hydrochloride); etc.

In certain aspects, specific drugs of interest include, but are not limited to: psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives); pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines (H1-antagonists, H2-antagonists), histamine metabolism drugs, (5) cardiovascular drugs, e.g. cardiotonics (plant extracts, butenolides, pentadienolids, alkaloids from erythrophleum species, ionophores, -adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like;

antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; b-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Name brand drugs of interest include, but are not limited to: Lovastatin™ drug, Enalapril™ drug, Prozac™ drug, Prilosec™ drug, Lipotor™ drug, Claritin™ drug, Zocor™ drug, Ciprofloxacin™ drug, Viagra™ drug, Crixivan™ drug, Ritalin™ drug, and the like.

Drug compounds of interest are also listed in: Goodman & Gilman's, The Pharmacological Basis of Therapeutics (9th Ed) (Goodman et al. eds) (McGraw-Hill) (1996); and 2001 Physician's Desk Reference.

Also of interest are analogs of the above compounds.

For all of the above active agents, the active agents may be present as pharmaceutically acceptable salts.

Also of interest as active agents are diagnostic agents. Diagnostic agents of interest include agents useful in fluorescence and X-ray diagnostic procedures, among others. Specific types of agents of interest include isotopic agents (for example radioactive dyes or metabolites), fluorescent agents, radio-opaque agents, etc.

The amount of active agent that is present in the IEM may vary. In some instances, the amount of active agent that is present in the membrane may range from 0.01 to 100% by weight.

IEM Manufacture

A variety of manufacturing protocols may be employed to produce aspects of the invention. The IEM and membrane components may be produced as described above. The IEM may be stably associated with the ingestible component in some manner. The IEM may be stably associated with the vehicle in a number of different ways, e.g., as described above. IEM fabrication protocols of interest include, but are not limited to, those described in PCT application serial nos. PCT/US2006/016370 and PCT/US08/77753; as well as in U.S. Provisional Application Ser. No. 61/142,849; the disclosures of which are herein incorporated by reference.

Systems

Also provided are systems that include an IEM and a detection component, e.g., in the form of a receiver. Receivers of interest are those that are configured to detect, e.g., receive, a communication from an IEM. The signal detection component may vary significantly depending on the nature of the communication that is generated by the IEM. As such, the receiver may be configured to receive a variety of different types of signals, including but not limited to: RF signals, magnetic signals, conductive (near field) signals, acoustic signals, etc. In certain aspects, the receiver is configured to receive a signal conductively from an IEM, such that the two components use the body of the patient as a communication medium. As such, communication that is transferred between IEM and the receiver travels through the body, and requires the body as the conduction medium. The IEM communication may be transmitted through and received from the skin and other body tissues of the subject body in the form of electrical alternating current (a.c.) voltage signals that are conducted through the body tissues. As a result, such aspects do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject.

The receiver may include a variety of different types of receiver elements, where the nature of the receiver element necessarily varies depending on the nature of the signal produced by the signal generation element. In certain aspects, the receiver may include one or more electrodes, e.g., 2 or more electrodes, 3 or more electrodes, and/or includes multiple, e.g., 2 or more, 3 or more, 4 or more pairs of electrodes, etc., for detecting communications associated with an IEM. In certain aspects, the receiver includes two or three electrodes that are dispersed at a distance from each other, e.g., a distance that allows the electrodes to detect a differential voltage. The distance between any two electrodes may vary, and in certain aspects ranges from about 0.1 to about 5 cm, such as from about 0.5 to about 2.5 cm, e.g., about 1 cm.

In addition to signal receiving elements, such as electrodes, receivers of the invention may include one or more integrated circuit components, one or more power components (such as power receivers or batteries), signal transmission components, housing components, etc.

The receivers of interest include both external and implantable receivers. In external aspects, the receiver is ex vivo, by which is meant that the receiver is present outside of the body during use. Where the receiver is implanted, the receiver is in vivo. The receiver is configured to be stably associated with the body, e.g., either in vivo or ex vivo, at least during the time that it receives communication from the IEM.

In certain aspects, the receiver is configured to provide data of a received signal to a location external to said subject. For example, the receiver may be configured to provide data to an external data receiver, e.g., which may be in the form of a monitor (such as a bedside monitor), a computer, a personal digital assistant (PDA), phone, messaging device, smart phone, etc. The receiver may be configured to retransmit data of a received communication to the location external to said subject. Alternatively, the receiver may be configured to be interrogated by an external interrogation device to provide data of a received signal to an external location.

Receivers of interest include, but are not limited to, those receivers disclosed in: PCT application serial nos. PCT/US2006/016370 published as WO 2006/116718; PCT/US2008/52845 published as WO 2008/095183; PCT/US2007/024225 published as WO 2008/063626 and PCT/US2008/085048; as well as U.S. Provisional Application Ser. No. 61/160,289; the disclosures of which applications (and particularly receiver components thereof) are herein incorporated by reference.

Systems of the invention may include an external device which is distinct from the receiver (which may be implanted or topically applied in certain aspects), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, phones, such as smart phones, computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Methods

Aspects of the invention further include methods of using IEMs, such as those described above. Methods of the invention generally include administering an IEM to a subject, e.g., by self-administration or via the assistance of another, such as a health care practitioner. Generally, methods of the invention will include placing the in the mouth of a subject such that the subject swallows the IEM. In this manner, the subject ingests the IEM. IEMs may be employed with a variety of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain aspects, the subjects will be humans.

Following ingestion, the methods include emitting one or more signals from the ingested IEM, for example when the IEM contacts the target physiological site. As reviewed above, the nature of the emitted signal may vary greatly. In some instances, the emitted signal is a conductively transmitted signal. Methods of the invention may also include receiving a signal emitted from an IEM, e.g., at a receiver, such as described above. In some instances, the received signal is a conductively transmitted signal.

IEMs may be employed in a variety of different applications. Applications of interest include, but are not limited to: monitoring patient compliance with prescribed therapeutic regimens; tailoring therapeutic regimens based on patient compliance; monitoring patient compliance in clinical trials; monitoring usage of controlled substances; monitoring the occurrence of a personal event of interest, such as the onset of symptoms, etc., and the like. Applications of interest are further described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753; the disclosures of which are herein incorporated by reference.

Kits

Also provided are kits that include one or more IEMs, such as described above. In those aspects having a plurality of IEMs, the IEMs may be packaged in a single container, e.g., a single tube, bottle, vial, and the like, or one or more dosage amounts may be individually packaged such that certain kits may have more than one container of IEMs. In certain aspects the kits may also include a receiver, such as reviewed above. In certain aspects, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging)

etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A device comprising:
   an ingestible event marker comprising:
      an identifier circuitry component that transmits a conductive signal through a body as a conductive medium when activated, where the conductive signal forms a current signature that identifies the ingestible event marker;
      a first electrochemical material electrically coupled to the identifier circuitry component;
      a second electrochemical material electrically coupled to the identifier circuitry at a different location from the first electrochemical material, where the second electrochemical material is dissimilar from the first electrochemical material such that the first and second electrochemical materials provide a voltage potential difference when in contact with a conductive fluid to power the identifier circuitry component and cause the identifier circuitry component to transmit a conductive signal through the conductive fluid; and
      an electrically insulative signal amplification element disposed between the first electrochemical material and the second electrochemical material, that extends beyond outer edges of the first electrochemical material and the second electrochemical material, such that the electrically insulative signal amplification element is configured to define a current path about the electrically insulative signal amplification element that is greater than a distance between the first electrochemical material and the second electrochemical material; and
   an osmotic ingestible component attached to the ingestible event marker, the osmotic ingestible component configured to provide the conductive fluid to the identifier circuitry of the ingestible event marker.

2. The device of claim 1, wherein the osmotic ingestible component comprises an osmotic member fabricated to absorb liquid and expand as it absorbs liquid.

3. The device of claim 2, wherein the osmotic ingestible component comprises a semipermeable layer;
the semipermeable layer substantially surrounding the osmotic member and forming an internal space; and
wherein the ingestible event marker is placed within the internal space formed by the semipermeable layer relative to the osmotic member, such that expansion of the osmotic member as it absorbs the conductive fluid causes the ingestible event marker to become exposed to the conductive fluid and power the identifier circuitry component.

4. The device of claim 1, wherein the osmotic ingestible component is a tablet.

5. The device of claim 1, wherein the osmotic ingestible component is an osmotic capsule comprising:
an outer semipermeable layer forming a passageway; and
an osmotic member attached to the outer semipermeable layer.

6. The device of claim 2 wherein the osmotic member is attached to the ingestible event marker.

7. The device of claim 5, wherein the ingestible event marker is configured as a barrier that separates the osmotic member from an active agent composition present in the osmotic capsule.

8. The device of claim 5, wherein the ingestible event marker is placed within the semipermeable layer relative to the osmotic member such that expansion of the osmotic member as it absorbs the conductive fluid causes the ingestible event marker to become exposed to the conductive fluid.

9. The device of claim 1, wherein the osmotic ingestible component comprises:
a liquid capsule comprising:
a shell; and
a liquid medium present in the shell.

10. The device of claim 9, wherein the ingestible event marker is in physical communication with the liquid medium.

11. The device of claim 10, further comprising a coating located on a portion of the ingestible event marker to protect the portion of the ingestible event marker from interacting with the liquid medium.

12. The device of claim 11, wherein the coating comprises a pH sensitive coating selected such that the coating interacts with the pH level of a specific environment in the body.

13. The device of claim 9, wherein the osmotic ingestible component further comprises a vesicle and wherein the ingestible event marker is physically located within the vesicle.

14. The device of claim 9, further comprising an encasing liquid to encase the ingestible event marker, wherein the encasing liquid is immiscible with the liquid medium.

15. The device of claim 9, wherein the shell further comprises a sealed compartment to house the ingestible event marker.

16. The device of claim 9, wherein the ingestible event marker is integrated with the shell.

17. A system comprising:
a device comprising:
an ingestible event marker comprising:
an identifier circuitry component that transmits a conductive signal when activated, where the conductive signal forms a current signature that identifies the ingestible event marker;
a first electrochemical material electrically coupled to the identifier circuitry component;
a second electrochemical material electrically coupled to the identifier circuitry at a different location from the first electrochemical material, where the second electrochemical material is dissimilar from the first electrochemical material such that the first and second electrochemical materials provide a voltage potential difference when in contact with a conductive fluid to power the identifier circuitry component and cause the identifier circuitry component to transmit a conductive signal through the conductive fluid; and
an electrically insulative signal amplification element disposed between the first electrochemical material and the second electrochemical material, that extends beyond outer edges of the first electrochemical material and the second electrochemical material, such that the electrically insulative signal amplification element is configured to define a current path about the electrically insulative signal amplification element that is greater than a distance between the first electrochemical material and the second electrochemical material; and
an osmotic ingestible component attached to the ingestible event marker, the osmotic ingestible component configured to provide the conductive fluid to the identifier circuitry; and
a receiver to detect the current signature as it is transmitted through an environment surrounding the device.

18. The system of claim 17, wherein the osmotic ingestible component comprises an osmotic member fabricated to absorb liquid and expand as it absorbs liquid.

19. The system of claim 17, wherein the osmotic ingestible component comprises:
a liquid capsule comprising:
a shell; and
a liquid medium present in the shell.

20. The system of claim 18, wherein the osmotic ingestible component comprises a semipermeable layer substantially surrounding the osmotic member and forming an internal space; and
wherein the ingestible event marker is placed within the internal space formed by the semipermeable layer relative to the osmotic member, such that expansion of the osmotic member as it absorbs the conductive fluid causes the ingestible event marker to become exposed to the conductive fluid and power the identifier circuitry component.

* * * * *